(12) United States Patent
San Gabriel et al.

(10) Patent No.: US 7,186,819 B2
(45) Date of Patent: Mar. 6, 2007

(54) GLUTAMATE RECEPTOR AND UTILIZATION THEREOF

(75) Inventors: Ana San Gabriel, Kawasaki (JP); Hisayuki Uneyama, Kawasaki (JP); Takami Maekawa, Kawasaki (JP); Kunio Torii, Kawasaki (JP)

(73) Assignee: Ajinomoto Co., Inc., Tokyo (JP)

( * ) Notice: Subject to any disclaimer, the term of this patent is extended or adjusted under 35 U.S.C. 154(b) by 24 days.

(21) Appl. No.: 10/918,857

(22) Filed: Dec. 10, 2004

(65) Prior Publication Data

US 2005/0282746 A1 Dec. 22, 2005

Related U.S. Application Data

(63) Continuation of application No. PCT/JP03/01496, filed on Feb. 13, 2003.

(30) Foreign Application Priority Data

Feb. 14, 2002 (JP) .............................. 2002-037278

(51) Int. Cl.
C12N 15/12 (2006.01)
(52) U.S. Cl. ................. 536/23.5; 435/69.1; 435/252.3; 435/320.1
(58) Field of Classification Search .................... None
See application file for complete search history.

(56) References Cited

FOREIGN PATENT DOCUMENTS

| EP | 0 569 240 A1 | 11/1993 |
| WO | 92/10583 A1 | 6/1992 |
| WO | 94/29449 A1 | 12/1994 |

OTHER PUBLICATIONS

Masu, M. et al., "Sequence and expression of a metabotropic glutamate receptor", *Nature*, vol. 349, pp. 760-765, (1991).
Houamed, K. M. et al., "Cloning, Expression, and Gene Structure of a G Protein-Coupled Glutamate Receptor from Rat Brain", *Science*, vol. 252, pp. 1318-1321, (1991).
Lindemann, B., "Receptors and transduction in taste", *Nature*, vol. 413, pp. 219-225, (2001).
Chaudhari, N. et al., "A metabotropic glutamate receptor variant functions as a taste receptor", *Nature Neuroscience*, vol. 3, No. 2, pp. 113-119, (2000).
Tanabe, Y. et al., "A Family of Metabotropic Glutamate Receptors", *Neuron*, vol. 8, pp. 169-179, (1992).
Flor, P. J. et al., "Molecular Cloning, Functional Expression and Pharmacological Characterization of the Human Metabotropic Glutamate Receptor Type 4", *Neuropharmacology*, vol. 34, No. 2, pp. 149-155, (1995).
Berk, M. et al., "Platelet Glutamate Receptor Supersensitivity in Major Depressive Disorder", *Clinical Neuropharmacology*, vol. 24, No. 3, pp. 129-132, (2001).
Karim, F. et al., "Metabotropic Glutamate Receptor Subtypes 1 and 5 Are Activators of Extracellular Signal-Regulated Kinase Signaling Required for Inflammatory Pain in Mice", *The Journal of Neuroscience*, vol. 21, No. 11, pp. 3771-3779, (2001).
Berk, M. et al., "The Specificity of Platelet Glutamate Receptor Supersensitivity in Psychotic Disorders", *Life Sciences*, vol. 66, No. 25, pp. 2427-2432, (2000).
Carlton, S. M. et al., "Inflammation-induced changes in peripheral glutamate receptor populations", *Brain Research*, vol. 820, pp. 63-70, (1999).
Haxhiu, M. A. et al., "The role of excitatory amino acids in airway reflex responses in anesthetized dogs", *Journal of the Autonomic Nervous System*, vol. 67, pp. 192-199, (1997).
Inagaki, N. et al., "Expression and role of ionotropic glutamate receptors in pancreatic islet cells", *The FASEB Journal*, vol. 9, pp. 686-691, (1995).
Erdö, S. L., "Excitatory amino acid receptors in the mammalian periphery", *TRENDS in Pharmacological Sciences*, vol. 12, pp. 426-429, (1991).
Aas, P. et al., "Stimulation of peripheral cholinergic nerves by glutamate indicates a new peripheral glutamate receptor", *European Journal of Pharmacology*, vol. 164, pp. 93-102, (1989).
Said, S. I. et al., "Glutamate signalling in the lung", *TRENDS in Pharmacological Sciences*, vol. 22, No. 7, pp. 344-345, (2001).
Skerry, T. M. et al., "Glutamate signalling in non-neuronal tissues", *TRENDS in Pharmacological Sciences*, vol. 22, No. 4, pp. 174-181, (2001).
Bray, G. A., "Afferent signals regulating food intake", *Proceeding of the Nutrition Society*, vol. 59, pp. 373-384, (2000).
Bray, G. A., "Nutrient Balance and Obesity: An Approach to Control of Food Intake in Humans", *Medical Clinics of North America*, vol. 73, No. 1, pp. 29-45, (1989).
Mei, N., "Recent studies on intestinal vagal afferent innervation. Functional implications", *Journal of the Autonomic Nervous System*, vol. 9, pp. 199-206, (1983).
Mei, N. et al., "Current data and ideas on digestive sensitivity", *Journal of the Autonomic Nervous System*, vol. 41, pp. 15-18, (1992).
Mei, N., "Intestinal Chemosensitivity", *The American Physiological Society*, vol. 65, No. 2, pp. 211-217, (1985).
Pin, J. et al., "Alternative splicing generates metabotropic glutamate receptors inducing different patterns of calcium release in *Xenopus* oocytes", *Proc. Natl. Acad. Sci. USA*, vol. 89, pp. 10331-10335, (1992).
Kasahara, J. et al., "Inositol phosopholipid metabolism in *Xenopus* oocytes mediated by endogenous $G_o$ and $G_i$ proteins", *Federation of European Biochemical Societies*, vol. 355, pp. 41-44, (1994).

(Continued)

*Primary Examiner*—John Ulm
(74) *Attorney, Agent, or Firm*—Nath Law Group PLLC; Gary M. Nath; Susanne M. Hopkins

(57) ABSTRACT

The inventive subject matter relates to a glutamate receptor, DNA which encodes the receptor, a transformed cell expressing the receptor, a method for producing the receptor, a method for identifying an agonist, antagonist, or allosteric modulator for glutamic acid, a method for identifying an agonist for glutamic acid, an antibody to the receptor, and processes for making glutamate receptor modulators and pharmaceutical compositions comprising said modulator.

6 Claims, 8 Drawing Sheets

OTHER PUBLICATIONS

Takahashi, K. et al., "Role of the Large Extracellular Domain of Metabotropic Glutamate Receptors in Agonist Selectivity Determination", *The Journal of Biological Chemistry*, vol. 268, No. 26, pp. 19341-19345, (1993).

Naples, M. A. et al., "Pharmacological profiles of the metabotropic glutamate receptor ligands [$^3$H]L-AP4 and [$^3$H]CPPG", *Neuropharmacology*, vol. 40, pp. 170-177, (2001).

Thomsen, C. et al., "Cloning and Characterization of a Metabotropic Glutamate Receptor, mGluR4b", *Neuropharmacology*, vol. 36, No. 1, pp. 21-30, (1997).

Adams, S. R. et al., "Fluorescence ratio imaging of cyclic AMP in single cells", *Nature*, vol. 349, pp. 694-697, (1991).

McConnell, H. M. et al., "The Cytosensor Microphysiometer: Biological Applications of Silicon Technology", *Science*, vol. 257, pp. 1906-1912, (1992).

Hermans, E. et al., "Structural, signalling and regulatory properties of the group I metabotropic glutamate receptors: prototypic family C G-protein-coupled receptors", *Biochem. J.*, vol. 359, pp. 465-484, (2001).

Niijima, A., "Effect of Oral and Intestinal Stimulation With Umami Substance on Gastric Vagus Activity", *Physiology & Behavior*, vol. 49, pp. 1025-1028, (1991).

mGluR1 Brain type Model mGluRTβ and mGluRTγ type Model mGluRTα type Model (1) Region of Body of the Stomach (Intrinsic Gastric Gland)
(2) Pyloric Region (Pyloric Gland)

① ②   : digested molecular marker

③ ④   : rat brain cDNA

⑤ ~ ⑩ : rat taste bud cDNA

PCR Primers Used:

mGluR1 718-3 (Forward)

mGluR1-3266   ( Reverse)

① λ-Eco T4 I digest molecular marker
② cDNA of Brain of Rat
③ cDNA of Brain of Rat
④ cDNA of Brain of Rat
⑤ cDNA of Brain of Rat
⑥ cDNA of Taste Bud of Rat
⑦ cDNA of Taste Bud of Rat
⑧ Φ x174-Hinc II digest of Molecular Weight Marker
⑨ Φ x174-Hae III digest of Molecular Weight Marker PCR Primers Used:
mGluR1-790-2 (Forward)
mGluR1-4198

GLUTAMATE RECEPTOR AND UTILIZATION THEREOF

This application is a Continuation of International Application No. PCT/JP03/01496, filed on 13 Feb. 2003 and claiming priority to Japanese Patent Application No. 2002-37278, filed 14 Feb. 2002.

TECHNICAL FIELD

The present invention relates to novel glutamate receptors and utilization thereof; more specifically to a glutamate receptor, DNA which encodes the receptor, a transformed cell expressing the receptor, a method for producing the receptor, a method for identifying an agonist, antagonist, or allosteric modulator for glutamic acid, a method for identifying an agonist for glutamic acid, an antibody to the receptor, and processes for making glutamate receptor modulators and pharmaceutical compositions comprising said modulator.

BACKGROUND ART

Human sense of taste is believed to be constituted of five basic tastes—salty, sweet, acidic, bitter and umami taste (relishable taste). Each taste is generated by the binding of a taste substances to each receptor specifically expressed in taste cells existing in taste buds of the tongue. Until now, ENaC/Deg. (salty taste receptor), EnaC, ASIC, HCN (acidic taste), T2R family (bitter taste receptor), T1R2/T1R3 (sweet taste receptor), Taste mGluR4 (umami taste receptor), etc. have been cloned as candidates of the taste receptors (As to details, refer to Lindemann, B., Nature, 413; 13, 219–225, 2001; the cited document is incorporated by reference in the present specification; that is the same hereinafter as well).

A low-affinity glutamate receptor expressed in taste bud cells in the rat found by Chaudhari, N., Landin, A. M., Roper, S. D., et al. as an umami taste receptor has been a convincing evidence for proving the umami taste-receiving mechanism at molecular level (*Nat. Neurosci.,* 2000, February; 3(2):113–9). The umami taste receptor has the same host gene as that in type 4 (mGluR4) which is a subtype of glutamate receptor of a rat brain type/a metabotropic type (Tanabe, Y., et al., *Neuron,* 1992, January; 8(1):169–79; Flor, P. J., et al., *Neuropharmacology,* 1995, February; 34(2): 149–55); and since taste type mGluR4 holds a partially deficient extracellular domain by a splicing variation, the finding of specific working substances other than glutamic acid that can utilize the present new type variant as a peripheral glutamate receptor has been receiving public attention.

Glutamic acid is a major excitatory neurotransmitter in the central nervous system, and it is widely accepted that its abnormal control is involved in progressive encephalopathies such as memory disorders, ischemic encephalopathy, amyotropic lateral sclerosis (ALS), Parkinson's disease, and Huntingon's chorea (Meldrum, B. S., Neurology, 1994 November; 44 (11 Supple 8):S14–23; Nishizawa, Y., Life Sci. 2001 June 15; 69(4):369–81). Therefore, many studies concerning glutamate receptors have been carried out up to now in cranial nerve system. Many receptors (three kinds of ionotropic receptors and eight kinds of metabotropic receptors) have been found in the central nervous system with their splicing variants as well. Particularly, since 1992 when metabotropic glutamate receptor type I (mGluR1a) was cloned by Nakanishi, et al., at least three splicing variants (mGluR1b, mGluR1c and mGluR1d) have been confirmed as mGluR1 variants (As to details, refer to Hermans, E. and Challiss, R. A., *Biochemical J.,* 359:465–484, 2001). In all of those variants, the C-terminal region of mGluR1a becomes short, and their existence in nerve cells and glia cells has been confirmed. On the basis of such abundant receptor information, development for working drugs which are specific to each receptor has been extensively carried out. Even today new therapeutic drugs in the treatment of the above-mentioned diseases are being developed (As to details, refer to Barnard, E. A., *Trends Pharmacol. Sci.,* 1997, May; 18(5):141–8; Schoepp, D. D., Conn. P. J., *Trends Pharmacol. Sci.,* 1993, January; 14(1):13–10).

Nowadays, we have several pieces of knowledge that suggest physiological functions of the peripheral glutamate receptor (Berk, M., Plein, H., Ferreira, D., Clin. Neuropharmacol., 2001, May–June; 24(129–32; Karim, F., J. Neurosci. 2001, Jun. 1; 21(11):3771–9; Berk, M., Plein, H., Belsham, B., Life Sci. 2000;66(25):2427–32; Carlton, S. M., Goggeshall, R. E., Brain Res. 1999, Feb. 27; 820(1–2):63–70; Haxhij. M. A., Erokwu, B., Dreshaj, I. A., J. Auton. Nerv. Syst. 1997, Dec. 11; 67(3):192–9; Inagaki, N., FASEB J. 1995, May; 9(8):686–91; Erdo, S. L., Trends Pharamcol. Sci., 1991, November; 12(11):426–9; Aas, P., Tanso, R., Fonnum, F., Eur. J. Pharamacol. 1989, May 2; 164(1): 93–102; Said, S. I., Dey, R. D., Dickman, K., Trends Pharmacol. Sci. 2001, July; 22(7):344–5; Skerry, T. M., Genever, P. G., Trends Pharamacol., Sci. 2001, April; 22(4): 174–81). However, those peripheral glutamate receptors are expressed in peripheral nerves, smooth muscle and immune tissues. There has been no report for their expression in epithelium of tongue and digestive tract. In mammals including humans to maintain normal growth and health, it is necessary to orally take up required amounts of nutrients at a specific timing and excrete disposable matter. This is actually done by the digestive tract, which is a single tube consisting of oral cavity, stomach, small intestine and large intestine. The process of digestion and absorption is controlled by intrinsic intestinal neuroplexus and extrinsic cranial nerves.

The judgment as to whether or not to take a necessary nutrient is the result of brain integration of a signaling pathway that the individual is aware of taste with an autonomous signaling pathway that the individual is unaware of visceral sense. It is considered that salty taste (sodium, potassium, etc.) serves as a marker of minerals and is required for maintaining the osmotic pressure of the body fluid; sweetness (glucose) serves as a marker of carbohydrates and is required for supplementing energy; umami (sodium glutamate) serves as protein marker and is useful for supplementing energy and essential amino acids; and bitterness serves as a marker for toxic substances. That is, necessary nutrients are taken up relying on the tastes thereof. Then, if necessary amounts are ingested, satiation is determined by a series of intracerebral processes coming from the signal input to the solitary tract nucleus. Those signals are derived from activated vagus afferent fibers through nutrient sensors existing in the stomach, small intestine, and hepatoportal vein (Bray, G. A., Proc. Nutr. Soc., 2000;59:373–84; Bray G. A., Med. Clin. North. Am. 1989:73:29).

On the other hand, physiological studies on the mechanism for chemical sensation in the digestive tract have been performed for a long time. It is supposed that there are sensors that detect the content of the digestive tract (for the details, reference is made to Mei, N., J. Auton. Nerv. Syst., 1983;9:199–206; Mei, N., Lucchini, S., J. Auton. Nerv. Syst., 1992;41:15–8). The digestive chemosensory system includes a glucose sensor (Mei, N., J. Physiol. (Lond.) 1978, 282, 485-5-6), a temperature sensor (El Ouazzani, T., Mei, N., Exp. Brain Res. 1979;15;34:419–34), an osmotic pressure sensor (Mei, N., Garnier, L., J. Auton. Nerv. Syst., 1986;16:159–70), a pH sensor, an amino acid sensor (Mei, N., Physiol. Rev., 1985;65:211–37), and a stretch sensor (Barber, W. D., Burks, T. F., Gastroenterol Clin. North. Am. 1987; 16:521–4).

In particular, a sensor that recognizes glutamic acid was suggested by Niijima et al. from neural excitation that occurred when glutamic acid was administered in the digestive tract. In this experiment, the technique of recording neural discharge activity was used for the stomach branch and abdominal cavity branch of the vagus nerve. Those vagal branches control mainly the stomach and small intestine and responded to glutamic acid; therefore was assumed that there is a mechanism that recognizes this amino acid at the vagus nerve ending (Niijima, A., Physiol. Behav., 1991; 49:1025–8).

DISCLOSURE OF THE INVENTION

Although many studies have been made on glutamate receptors and digestive tract sensors as described above, to date, glutamate perception is unclear and no progress has been made in recent works. Failure of receptor isolation from tissues containing glutamate sensors (receptor, transporter, etc.) necessary for nutrient recognition in the mucous membrane of the digestive tract prevented the progress in this research field. The inventors of the present invention expect that elucidation of the umami-like substances that bind to glutamate sensors in the digestive tract would enable development of drugs and the like directed to control of the nutrient recognition mechanism described below.

That is, the nutrient recognition mechanism also plays an important role on satiety or surfeit and improves poor physical condition in edacity and imbalance when indulging nutrients in eating disorders. It is considered that abnormal recognition of nutrients in the digestive tract naturally results in disturbance in the overall process of digestion and absorption, thus causing edacity, eating disorders, inappetence, indigestion, diarrhea, constipation, etc. Medically, there are many factors involved in the development of digestive diseases such as ulcers (stomach ulcer, duodenum ulcer) due to psychogenetic hyperphagia, cibophobia, obesity, anomaly of acid secretion, anomaly of blood flow in digestive tract, anomaly of secretion of digestive enzymes, etc., stress ulcers, drug-caused (NSAIDs, etc.) acute ulcers, ischemic ulcer (ischemic colitis), diabetes due to anomaly of secretion of insulin or anomaly of secretion of digestive tract hormone, heavy stomach, nausea, constipation, diarrhea, hypersensitivity bowel syndrome, etc. due to anomaly of gastrointestinal motility and so forth.

Further, in recent years, the abrupt increase in obesity incidence is a social phenomenon. Many of those who are obese are said to have decreased basal metabolism and tend to eat too much. How to control the appetite of obese individuals is of great social concern. Many try to be on an excessive diet. However, in most cases, they are unsuccessful. Thus, improving the mechanism of nutrient recognition in the digestive tract and achieving satiety with a normal meal is very important to those who are obese.

The second object of the present invention is derived from the above-mentioned viewpoint, and the matter to be solved is identification of an actual glutamate-like substance which binds to glutamate sensors in the epithelium of the tongue and the digestive tract and methods for utilizing such sensors are provided.

The present inventors have investigated a receptor distribution in the epithelium of the tongue and in the digestive tract by way of an immunohistological methods using antibodies that recognize the intracellular domain of the metabotropic glutamate receptor type 1 (mGluR1). As a result, it has been found that cells in the epithelium of the tongue and the mucous membrane layer of the stomach are positive for mGluR1 where the receptor is present. In the tongue epithelium, the apical site of taste cells from taste buds are positive for mGluR1. Whereas in the stomach, mucus-secreting cells (neck mucus cells) and pepsinogen-secreting cells (chief cells) at the body of the stomach and mucous cells at the antrum of the stomach are positive for mGluR1. cDNA cloning from tongue epithelium was successfully performed, which has produced a novel glutamate receptor. It is expected that this glutamate receptor is a novel umami taste receptor or a digestive tract glutamate sensor which was previously unknown and that the receptor cDNA, a purified receptor, and the receptor-expressing cells are useful for screening for modulators of umami taste receptor and digestive tract glutamate sensor.

The present invention has been achieved on the basis of the above findings and its summary is as follows.

(1) A glutamate receptor protein comprising:

(A) a transmembrane domain and an intracellular domain common to the type 1 metabotropic glutamate receptor; and (B) an extracellular domain which is shorter than type 1 metabotropic glutamate receptor by 481 or 409 amino acid residues.

(2) The glutamate receptor protein according to (1), wherein it is expressed on epithelium of tongue of rat.

(3) The glutamate receptor protein according to (1), wherein it has an amino acid sequence represented by SEQ ID NO: 6 and NO: 8 or an amino acid sequence represented by amino acid nos. 73 to 790 and 73 to 497 in the above amino acid sequence.

(4) The glutamate receptor protein according to (3), wherein it contains substitution, deletion, insertion or addition of one or plural amino acid residue(s) and is able to generate a second messenger by binding with glutamic acid.

(5) DNA which codes for the glutamate receptor protein mentioned in any of (1) to (4) and does not express the type 1 metabotropic glutamate receptor protein.

(6) A cell which holds DNA coding for the glutamate receptor protein mentioned in any of (1) to (4) in an expressible form.

(7) A method for the manufacture of a glutamate receptor protein, characterized in that, cells which hold DNA coding for the glutamate receptor protein mentioned in any of (1) to (4) in an expressible form are incubated in a medium whereupon the glutamate receptor protein is produced and then the glutamate receptor protein is collected from the above-mentioned cells.

(8) A method for the search of agonist, antagonist or allosteric modulator for glutamic acid, characterized in that, the glutamate receptor protein mentioned in any of (1) to (4) is made to react with a substance which binds to that protein in the presence of a substance to be tested whereupon inhibition or promotion of the reaction is detected.

(9) A method for the search of agonist for glutamic acid, characterized in that, the glutamate receptor protein mentioned in any of (1) to (4) is made to react with a substance to be tested whereupon the reaction is detected.

(10) The method according to (8), wherein the glutamate receptor protein from the cell of (6) or a membrane fraction prepared from the cell is used.

(11) The method according to (10), wherein inhibition or promotion of the above binding is detected by a second messenger generated by the glutamate receptor protein.

(12) The method according to (9), wherein the glutamate receptor protein from the cell of (6) or a membrane fraction prepared from the cell is used.

(13) The method according to (12), wherein inhibition or promotion of the above binding is detected by a second messenger generated by the glutamate receptor protein.

(14) An antibody which specifically binds to the glutamate receptor protein mentioned in any of (1) to (4).

(15) A method for the manufacture of a drug for the adjustment of a second messenger which is generated by binding of glutamic acid to a glutamate receptor comprising a step where the glutamate receptor protein mentioned in any of (1) to (4) is made to react with a substance which binds to said protein in the presence of a substance to be tested to detect inhibition or promotion of the reaction whereby agonist, antagonist or allosteric modulator for glutamic acid is searched and a step where a pharmaceutical composition is prepared using the agonist, antagonist or allosteric modulator for glutamic acid prepared in the above step as an effective ingredient.

(16) A method for the manufacture of a drug for the adjustment of a second messenger which is generated by binding of glutamic acid to a glutamate receptor comprising a step where the glutamate receptor protein mentioned in any of (1) to (4) is made to react with a substance to be tested to detect inhibition or promotion of the reaction whereby agonist for glutamic acid is searched and a step where a pharmaceutical composition is prepared using the agonist for glutamic acid prepared in the above step as an effective ingredient.

The present invention will now be illustrated in detail as hereunder.

Typically, the glutamate receptor protein of the present invention is any of a protein having an amino acid sequence represented by amino acid nos. 1 to 718 in the SEQ ID NO: 2 in the Sequence Listing, a protein having an amino acid sequence represented by amino acid nos. 1 to 425 in the SEQ ID NO: 4 in the Sequence Listing, a protein having amino acids 1 to 790 in the SEQ ID NO: 6 in the Sequence Listing and a protein having amino acids 1 to 497 in the SEQ ID NO: 8 in the Sequence Listing. An open reading domain of a base sequence of rat cDNA coding for the present protein is shown in SEQ ID NOS: 1, 3, 5, 7, 9 and 10.

Since a variant of the glutamate receptor protein as such is a metabotropic glutamate type 1 receptor (mGluR1) of a taste type found from epithelial cells of tongue, the present inventors named it as mGluRT; further, in view of homology of the sequences, the protein coded by SEQ ID NOS: 1 and 3 was named mGluRTα, the protein coded by SEQ ID NOS: 5 and 7 was named mGluRTβ and the protein coded by SEQ ID NOS: 9 and 10 was named mGluRTγ. In mGluR1, there have been known two types, i.e. type A (mGluR1a) and type B (mGluR1b), depending upon the splicing variation of C-terminal, and in the proteins of the present invention, proteins coded by SEQ ID NOS: 1 and 3, 5 and 7 and 9 and 10 are also variants corresponding to type A and type B, respectively. So the protein coded by SEQ ID NO: 1 was named mGluRTαa; the protein coded by SEQ ID NO: 3 was named mGluRTαb; the protein coded by SEQ ID NO: 5 was named mGluRTβa; the protein coded by SEQ ID NO: 7 was named mGluRTβb; the protein coded by SEQ ID NO: 9 was named mGluRTγa; and the protein coded by SEQ ID NO: 10 was named mGluRTγb. Hereinafter, the glutamate receptor proteins of the present invention may be generally referred to as mGluR1 variants in the present specification. When an appropriate promoter is linked to upstream region of the base sequences represented by SEQ ID NOS: 1, 3, 5, 7, 9 and 10 and is expressed within an appropriate cells, it is possible to produce active glutamate receptors.

Comparison of the amino acid sequence of the present invention with that of brain-type metabotropic glutamic type 1 receptor (hereinafter referred to as mGluR1) which has been confirmed to be present in the brain is shown in FIG. 1. The C-terminal side of mGluRTαa (amino acid numbers 1 to 718 in SEQ ID NO: 2) is identical with each C-terminal side of mGluR1a, and the C-terminal side of mGluRTαb (amino acid numbers 1 to 425 in SEQ ID NO: 4) is identical with C-terminal side of mGluR1b, respectively; but as compared with mGluR1, both N-terminal side were shorter to an extent of 481 amino acid residues. On the other hand, mGluRTβ and mGluRTγ had the same coding regions, and in both of them, C-terminal sides (amino acid numbers 1 to 790 in SEQ ID NO: 6) of type A (mGluRTβa and mGluRTγa) are identical with that of mGluR1a; while, C-terminal sides (amino acid numbers 1 to 497 in SEQ ID NO: 8) of type B (mGluRTβb and mGluRTγb) are identical with that of mGluR1b; but, as compared with mGluR1, N-terminal side was shorter to an extent of 409 amino acid residues. As will be mentioned later, it is believed that the glutamate receptor of the present invention is a splicing variant derived from gene which is common to mGluR1. Hereinafter, the glutamate receptor protein may be wholly called as mGluR1 variants in the present specification.

When the cDNA sequence coding for mGluR1 variants are compared with mGluR1 mRNA sequence, it was suggested that they were derived from common gene. Thus, mGluR1 variants are presumed to be the result where exon in mGluR1 gene was deleted by an alternative splicing. The detail is shown in FIG. 1. Brain-type mGluR1 comprises exons 1 to 9; and for subtypes, type A (mGluR1a) comprises exons 1 to 7 and 9, and type B (mGluR1b) comprises exons 1 to 8 (refer to FIG. 1A). On the other hand, among mGluR1 variants of the present invention, mGluRTαa comprises exons 5 to 7 and 9, mGluRTαb comprises exons 5 to 8 (refer to FIG. 1B), mGluRTγa comprises exons 3 to 7 and 9, mGluRTβb comprises exons 3 to 8, mGluRTγa comprises exons 4 to 7 and 9, and mGluRTγb comprises exons 4 to 8 (refer to FIG. 1C). Since initiation methionine codon is not present in exon 3 constituting mGluRTβ, coding region of mGluRTβ starts from methionine in exon 4; as a result, coding regions of mGluRTβ and mGluRTγ are common. Here, exons 1 to 6, exon 7 and exons 8 to 9 correspond to extracellular domain, seven transmembrane domain and intracellular domain, respectively.

FIG. 2 shows the structures of mGluR1 and mGluR1 variants. mGluR1 comprises intracellular domain (exons 1 to 6), seven transmembrane domain (exon 7) and extracellular domain (type A: exon 9; type B: exon 8). mGluR1 variants also have the same intracellular domain and seven transmembrane domain as mGluR1 has, and it has the same sequence as those of mGluR1.

Incidentally, mGluRTα starts from exon 5; therefore, the amino acid sequence of SEQ ID NO: 2 (mGluRTαa) corresponds to 73 to 790 of the amino acid sequence in SEQ ID NO: 6 (mGluRTβa and mGluRTγa), and the amino acid sequence of SEQ ID NO: 4 (mGluRTαb) corresponds to 73 to 497 of the amino acid sequence in SEQ ID NO: 8 (mGluRTβb and mGluRTγb).

Thus, the mGluR1 variants of the present invention have the same transmembrane domain and intracellular domain as those of type 1 metabotropic glutamate receptor protein and has extracellular domain which is shorter to an extent of 409 or 481 amino acid residues than type 1 metabotropic glutamate receptor protein. Thus, the mGluR1 variant of the present invention is different from mGluR1 in terms of extracellular domain which is an acting site to ligand; therefore, it is presumed to be different from mGluR1 in terms of affinity to ligand. Meanwhile, it is common to mGluR1 in intracellular domain which is an effector domain of seven transmembrane G protein conjugate receptor (GPCR); therefore, it is a functional receptor which is able to generate a second messenger.

The mGluR1 variant of the present invention may be derived from a rat. Alternatively, so long as it can generate a second messenger when glutamic acid is bound thereto, the mGluR1 variant may be derived from any animal including mammalian such as human, monkey, mouse, dog, cow, and rabbit, birds, and fin. In the case where the mGluR1 variant is used as a component of pharmaceutical composition, it is preferably derived from a mammalian.

The mGluR1 variant of the present invention may be a protein having the amino acid sequence of SEQ ID NO: 6 or the amino acid sequence consisting of amino acid numbers 73 to 790 in SEQ ID NO: 6 (SEQ ID NO: 2), a protein having the amino acid sequence of SEQ ID NO: 8 or the amino acid sequence consisting of amino acid numbers 73 to 497 in SEQ ID NO: 8 (SEQ ID NO: 4), or a protein having the amino acid sequence of any of SEQ ID NOS: 2, 4, 6 and 7 including substitution, deletion, insertion or addition of one or a plurality of sites so long as it has properties of generating a second messenger when glutamic acid is bound thereto.

The "plurality" as used herein varies depending on the positions of amino acid residues in the three-dimensional structure of the protein and the types of the amino acids, however, the number may be such that the homology with the amino acid sequence shown by any of SEQ ID NOS: 2, 4, 6 and 8 is 80% or more, preferably 90% or more. More particularly, the plurality is 2 to 115, preferably 2 to 58, more preferably 2 to 30.

The glutamate receptor of the present invention may be in a purified or isolated form; however, when the activity is required, it is preferably in a form that is expressed in a suitable cells and localized in the membrane of the cell or in a form contained in a membrane fraction prepared from a cell in which the mGluR1 variant was expressed. Thus, the glutamate receptor of the present invention also includes cells that express mGluR1 variant or a membrane fraction prepared from such cells.

The mGluR1 variant can be obtained, for example, by introducing DNA that encodes the mGluR1 variant into a suitable host cell to express the mGluR1 variant. The above-mentioned DNA includes gene that encodes the mGluR1 variant, isolated from the chromosome of a cell of a mammalian such as mouse. When chromosomal gene is used, it is preferable that cDNA is used since it is considered necessary to control a post-transcriptional process such as splicing so that mGluR1 variant can be generated.

The cDNA of mGluR1 variant can be cloned by amplifying the cDNA of mGluR1 variant using RNA prepared from the epithelium of tongue of a mammal such as a rat as a template, and oligonucleotides shown in the embodiments as primers. In addition, since the structure of mGluR1 variant, particularly unique structure on the N-terminal region has been made clear by the present invention, cloning and identification of the cDNA of mGluR1 variant can be performed easily based on the structures. The open reading frame nucleotide sequence of the thus obtained cDNA of mGluR1 variant is shown in each SEQ ID NOS: 1, 3, 5, 7, 9 and 10.

Thus, another feature of the present invention is a polynucleotide coding for any of mGluR1 variants of the present invention. With regard to the polynucleotide coding for any of mGluR1 variants of the present invention, anything which contains a base sequence (DNA or RNA, preferably DNA) coding for the above-mentioned mGluR1 variant of the present invention may be used provided that it does not code for brain-type mGluR1. Such a polynucleotide is DNA and RNA such as mRNA coding for the mGluR1 variant of the present invention and may be double- or single-stranded. In the case of a double-stranded one, it may be a double-stranded DNA, a double-stranded RNA or a hybrid of DNA:RNA. In the case of a single-stranded one, it may be sense chain (code chain) or anti-sense chain (non-code chain). Typically, the polynucleotide is a polynucleotide having base sequences represented by SEQ ID NOS: 1, 3, 5, 7, 9 and 10.

The DNA which encodes the mGluR1 variants includes in addition to the nucleotide sequence shown in SEQ ID NOS: 1, 3, 5, 7, 9 and 10, DNA which hybridizes with DNA having this nucleotide sequence or a probe that can be prepared from the same nucleotide sequence under stringent conditions and that encodes the mGluR1 variant. The "stringent conditions" means conditions whereby specific hybrid is formed but nonspecific hybrids are not formed. It is difficult to clearly express the conditions by numeric values; examples thereof include those conditions whereby DNAs having high homology, for example, DNAs having 50% or more, preferably 75% or more homology hybridize with each other but DNAs having a lower homology than that will not hybridize with each other, or those conditions whereby DNAs hybridize with each other under ordinary washing conditions in southern hybridization, i.e., at 60° C. and a salt concentration corresponding to 1×SSC, 0.1% SDS, preferably 0.1×SSC, 0.1% SDS.

Cells to which DNA encoding the mGluR1 variant is introduced include preferably animal cells, insect cells or yeast when the activity of mGluR1 variant is necessary, with animal cells being particularly preferable. Examples of cells that are considered to enable transient expression of the function by introducing a recombinant vector containing DNA encoding the mGluR1 variant include *Xenopus laevis* oocyte, Chinese hamster ovary (CHO) cell, baby hamster kidney (BHK) cell, human embryonic kidney (HEK) cell, Sf-9 insect cell, PC12 cell, and COCA-2 cell. In addition, when DNA encoding the mGluR1 variant is incorporated in chromosomal DNA to express the mGluR1 variant permanently, those cells other than the *Xenopus laevis* oocyte are suitable.

With regard to a method for introduction of DNA coding for mGluR1 variant, publicly known methods may be used. Technique which is necessary for the operations such as an operation of introduction of DNA into cells is mentioned in Sambrook, J., Fritsch, E. F. and Maniatis, T. "Molecular Cloning, A Laboratory Manual, Second Edition", Cold Spring Harbor Laboratory Press (1989), etc.

On the other hand, when no physiological activity is necessary such as the case where the mGluR1 variant is used as an immunogen for preparing antibody that specifically binds to the mGluR1 variant, cells to which DNA encoding the mGluR1 variant is introduced may be those cells that do not express the mGluR1 variant in an active form. As such cells, microbial cells that are usually used for the production of heterologous protein, including *Escherichia coli* may be used.

To produce the mGluR1 variant in the host cell, DNA, which encodes the mGluR1 variant, is ligated to an expression regulation sequence such as promoter or enhancer suitable for the host cell. The DNA which encodes the mGluR1 variant may include a processing information site, for example, a ribosome binding site, an RNA splicing site, a polyadenylation site, and a transcription terminator sequence as necessary. Preferable expression control sequences include promoters derived from immunoglobulin gene, SV40, adenovirus, bovine papilloma virus, and cytomegalovirus.

The techniques necessary for the manipulation of cells such as introduction of DNA therein are described in, for example, Sambrook, J., Fritsch, E. F., and Maniatis, T., "Molecular Cloning A Laboratory Manual, Second Edition", Cold Spring Harbor Laboratory Press, (1989).

The mGluR1 variant and a cell that retains the mGluR1 variant can be produced by cultivating a cell that harbors the DNA encoding the mGluR1 variant obtained as described above in an expressible form in a medium to produce the mGluR1 variant.

Active mGluR1 variant, that is, mGluR1 variant that can generate a second messenger when glutamic acid is bound thereto can be utilized for screening agonist, antagonist or allosteric modulator of glutamic acid. For example, the mGluR1 variant and a substance that binds to the mGluR1 variant are reacted in the presence of a test substance, and inhibition or promotion of the reaction is detected, thereby screening agonist, antagonist or allosteric modulator of glutamic acid (hereinafter, these may be referred to collectively as "ligand"). The allosteric modulator binds to a site other than the binding site between the mGluR1 variant and glutamic acid to exhibit similar function to that of the agonist or antagonist.

Further, the agonist of glutamic acid may be screened by reacting the mGluR1 variant with a test substance and detecting the reaction.

The active mGluR1 variant may include cells that express the mGluR1 variant or membrane fractions prepared from such cells. Such membrane fractions may be prepared by allowing cells to express active mGluR1 variant, ultrasonically disrupting the cells, and subjecting the sonicate to density gradient centrifugation to collect a membrane fraction.

Further, examples of the substance that binds to the above-mentioned mGluR1 variant include glutamic acid, glutamic acid agonist, or known ligands that bind to mGluR1 (L-AP4, CPPG, MAP-4, or the like). The substances that modulate the activity of the mGluR1 variant include drugs that influence the intracellular concentration of calcium (calcium channel and sodium channel opener, Na/K pump inhibitor, Na/Ca exchange agonist, Ca-ATPase inhibitor, protein kinase C agonist), drugs that influence intracellular cAMP concentration (phosphodiesterase agonist, adenylate cyclase agonist), and drugs that influence intracellular cGMP concentration (cGMP-dependent phosphodiesterase agonist, guanylate cyclase agonist) and so forth.

Inhibition or promotion of the reaction between mGluR1 variant and a substance that binds thereto can be detected by measuring a second messenger that is generated by binding of a ligand such as glutamic acid to the mGluR1 variant. Alternatively, the above-mentioned inhibition or promotion of reaction can also be detected by measuring the binding of a labeled known ligand to the mGluR1 variant instead of detecting the second messenger.

Further, the reaction between the mGluR1 variant and the agonist of glutamic acid can be detected by detecting a second messenger that is generated by binding of the mGluR1 variant to the agonist of glutamic acid.

The intracellular domain of mGluR1 variant is the same as the brain type and gustatory bud type mGluR1 and the brain type and gustatory bud type mGluR1 have the same intracellular signal transmitting mechanism. Accordingly, the above-mentioned second messenger is a rise in intracellular calcium concentration accompanied by the production of inositol triphosphate (IP3) as a result of activation of Gq (GTP binding protein) followed by activation of phospholipase C. In the downstream area of calcium variation in signal transmittance, there are function adjustment of acute stage by phosphorylation of cytoplasm and membrane protein and that by gene expression adjustment via intracellular calcium-dependent protein kinase. Therefore, it is possible to detect a second messenger other than IP3 and calcium by measurement of intracellular cAMP, cGMP changes and channel function change as a result of activation of calcium-dependent phosphodiesterase, protein phosphorylation of cell membrane fraction, etc.

Hereinafter, specific methods for searching a ligand using mGluR1 variant will be exemplified.

(1) mGluR1 variant cRNA is expressed in oocytes of *Xenopus* and a ligand acting on mGluR1 variant is searched by a two-electrode voltage cramp method using increase or decrease in intracellular calcium-depending chloride current (Pin, J. P., et al., *Proc. Natl. Acad. Sci. USA,* 1992 Nov. 1; 89(21):10331–5; Kasahara, J., Sugiyama, H., *FEBS Lett.,* 1994 Nov. 21; 355(1):41–4; Takahashi, K., et al., *J. Biol. Chem.,* 1993 Sep. 15; 268)26):19341–5).

(2) A candidate compound for ligand and known ligand acting on mGluR1 (such as glutamic acid, quisqualic acid, CHPG, MPEP, LY367385, etc.) are acted on a mGluR1 variant-expressing cell or a membrane fraction prepared from that cell for a certain period and amount of the known ligand bound to cell membrane of the mGluR1 variant-expressing cell or the membrane fraction is measured to conduct a ligand search (Naples, M. A., *Neuropharmacology,* 2001;40(2):170–7; Thomsen, C., *Neuropharmacology,* 1991 January; 36(1):21–30; H. I. Yamamura, S. J. Enna and M. J. Kuhar, eds. 1958, Neurotransmitter Receptor Binding, 2nd ed., Raven Press, New York). Amount of the known ligand is able to be measured by the amount of radioactivity bound to the cell membrane or the membrane fraction after a radioactive labeling of a part of such substances.

(3) A calcium-sensitive dye (for example, Fura-2, Indo-1, Fluo-3 or the like) is introduced into an mGluR1 variant expressing cell in advance, and a ligand candidate compound and the mGluR1 variant expressing cells are allowed to contact for a certain period of time, and then ligands are screened by using as an index a change in a ratio of intensities of fluorescence (intracellular calcium concentration). Alternatively, screening of ligand is performed by a change in a ratio of intensities of fluorescence (intercellular calcium concentration) obtained when an mGluR1 variant agonist, a candidate compound for ligand, and an mGluR1 variant expressing cells into which a calcium-sensitive dye is introduced are allowed to contact for a certain period of time.

(4) Screening of ligands is performed by using as an index a change in a ratio of intensities of fluorescence (intracellular cAMP concentration) obtained when a cAMP-sensitive fluoroprotein (for example, FICRhR or the like) is introduced into an mGluR1 variant expressing cell in advance and then a ligand candidate compound and the mGluR1 variant expressing cells are allowed to contact for a certain period of time (Adams S R, Nature 1991 Feb. 21; 349(6311): 694–7).

(5) Screening of ligands is performed by using as an index the production amount of proton obtained when a candidate compound for ligand and an mGluR1 variant expressing cells are allowed to contact for a certain period of time, or when an mGluR1 variant agonist, a candidate compound for ligand and an mGluR1 variant expressing cells are allowed to contact for a certain period of time and measured by a cytosensor (McConnell H M, Science 1992 Sep. 25; 257 (5078):1906–12).

A food additive containing agonist, antagonist or allosteric modulator of glutamic acid searched as mentioned above as an effective ingredient is able to be used as a novel umami taste-adjusting substance. Further, a pharmaceutical composition containing agonist, antagonist or allosteric modulator of glutamic acid searched as mentioned above as an effective ingredient is able to be used as a drug for the adjustment of second messenger generated by binding of glutamic acid to a glutamate receptor. When the second messenger is adjusted, it is now possible that diseases and symptoms caused by abnormality of the glutamate receptor are improved and prevented.

The anomalies of control of vagus nerve include anomaly of afferent pathway (disorder of nutrient recognition) and anomaly of efferent pathway. The diseases or pathology due to the anomaly of afferent pathway include hyperphagia, cibophobia, obesity and so on. On the other hand, those due to the anomaly of efferent pathway include digestive ulcers (stomach ulcer, duodenum ulcer) due to psychogenetic hyperphagia, cibophobia, obesity, anomaly of acid secretion, anomaly of blood flow in digestive tract, anomaly of secretion of digestive enzymes, etc., stress ulcers, drug-caused (NSAIDs, etc.) acute ulcers, ischemic ulcer (ischemic colitis), diabetes due to anomaly of secretion of insulin or anomaly of secretion of digestive tract hormone, heavy stomach, nausea, constipation, diarrhea, hypersensitivity vowel syndrome, etc. due to anomaly of motility and so forth.

Use of mGluR1 variant as an immunogen enables preparation of an antibody that specifically binds to the mGluR1 variant. In particular, since the mGluR1 variant has a novel amino acid sequence in the N-terminus, antibody, particularly monoclonal antibody, that contains this portion as an epitope is expected to bind to the mGluR1 variant and not to bind to other glutamate receptors. The antibody specific to the mGluR1 variant can be used in immunostaining specific to the mGluR1 variant. Further, when the amino acid residue of the novel N-terminal intracellular domain (cell surface exposure part) is estimated from the three-dimensional structure forecast, it is possible to prepare an mGluR1 variant-specific antibody. An antibody which is specific to mGluR1 variant is able to be used for an immunostaining which is specific to mGluR1 variant, etc.

DETAILED DESCRIPTION OF THE INVENTION

Figure 1A:
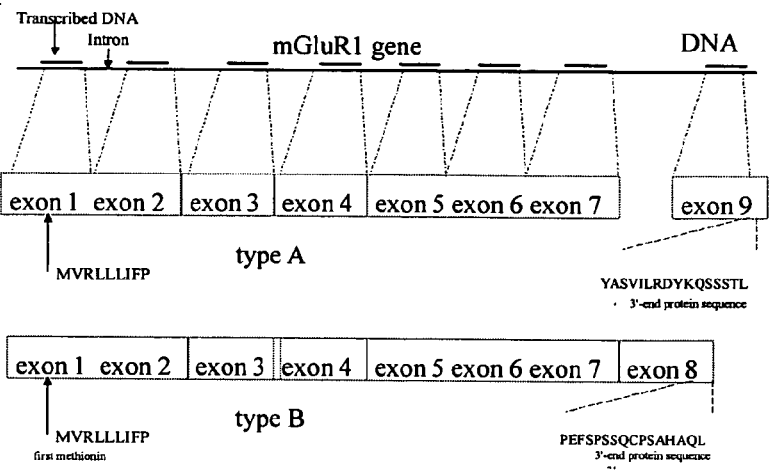
FIG. 1 is a graph which shows an outline of splicing of mGluR1 and mGluR1 variants (mGluRTα, mGluRTβ and mGluRTγ).
Figure 1B:
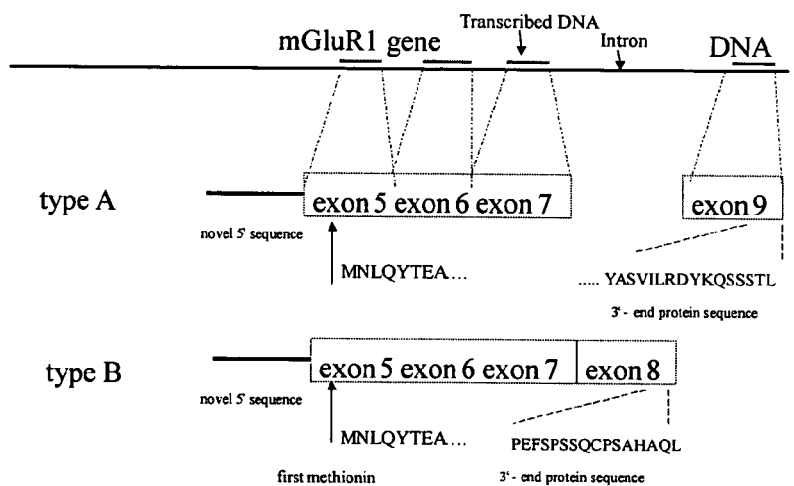
Figure 1C:
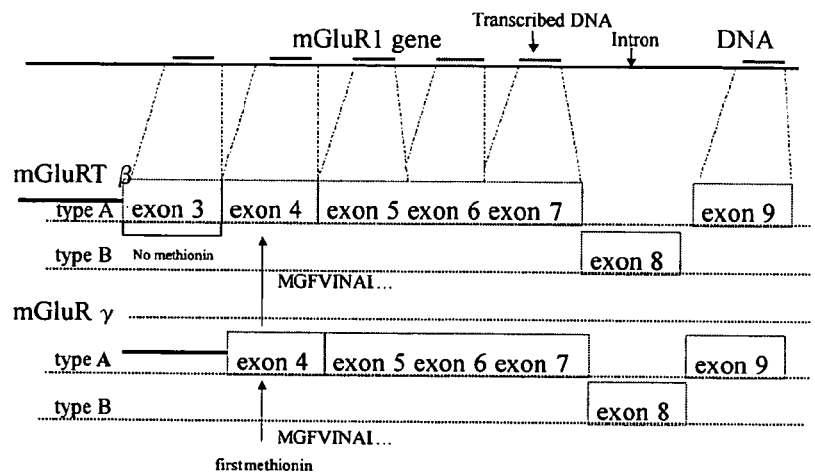
Figure 2:
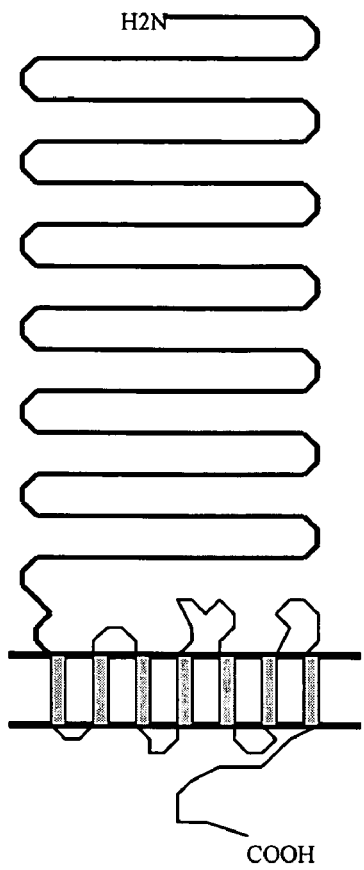
FIG. 2 is a graph which shows an outline of structures of mGluR1 and mGluR1 variants (mGluRTα, mGluRTβ and mGluRTγ).
Figure 2:
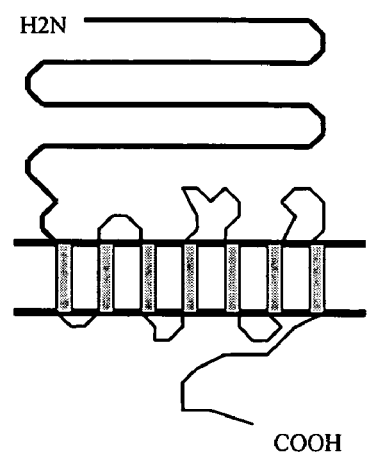
Figure 2:
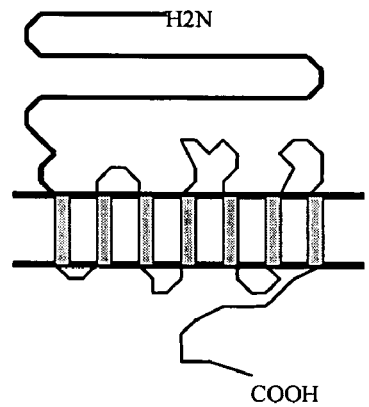

The present invention will now be more specifically illustrated by way of the following Examples although the present invention is not limited thereto.

The present inventive subject matter relates to a glutamate receptor protein comprising:

(a) a transmembrane domain and an intracellular domain common to the type 1 metabotropic glutamate receptor; and (b) an extracellular domain which is shorter than type 1 metabotropic glutamate receptor by between 409 and 481 amino acid residues.

In one aspect of the inventive subject matter, said glutamate receptor protein is expressed on rat tongue epithelium.

In a preferred embodiment, said glutamate receptor protein has an amino acid sequence represented by SEQ ID NO: 6. In another preferred embodiment, said glutamate receptor protein has an amino acid sequence represented by amino acid nos. 73 to 790 in SEQ ID NO: 6.

In a further preferred embodiment, said glutamate receptor protein has an amino acid sequence represented by SEQ ID NO: 8. In yet another preferred embodiment, said glutamate receptor protein has an amino acid sequence represented by amino acid nos. 73 to 497 in SEQ ID NO: 8.

The inventive subject matter further relates to an isolated DNA molecule which codes for a glutamate receptor protein comprising:

(a) a transmembrane domain and an intracellular domain common to the type 1 metabotropic glutamate receptor; and (b) an extracellular domain which is shorter than type 1 metabotropic glutamate receptor by between 409 and 481 amino acid residues, and which does not express the type 1 metabotropic glutamate receptor protein.

In a preferred embodiment, said isolated DNA molecule comprises a sequence of SEQ ID NO: 5.

In another preferred embodiment, said isolated DNA molecule comprises a sequence of SEQ ID NO: 7.

The inventive subject matter also relates to a cell transformed with an isolated DNA molecule coding for a glutamate receptor protein, comprising:

(a) a transmembrane domain and an intracellular domain common to the type 1 metabotropic glutamate receptor; and (b) an extracellular domain which is shorter than type 1 metabotropic glutamate receptor by between 409 and 481 amino acid residues, in an expressible form.

In one aspect of the inventive subject matter, said isolated DNA molecule in an expressible form further comprises a vector.

The inventive subject matter also relates to a method for producing a glutamate receptor protein, comprising the steps of:

(a) incubating a host cell transformed with DNA coding for a glutamate receptor protein comprising:

(i) a transmembrane domain and an intracellular domain common to the type 1 metabotropic glutamate receptor; and (ii) an extracellular domain which is shorter than type 1 metabotropic glutamate receptor by between 409 and 481 amino acid residues, in an expressible form, in a medium wherein said glutamate receptor protein is expressed; and (b) collecting said expressed glutamate receptor protein from said host cells.

The inventive subject matter additionally relates to a method for identifying an agonist, antagonist, or allosteric modulator for glutamic acid, comprising the steps of:

(a) in the presence of a substance to be tested, reacting a glutamate receptor protein comprising:

(i) a transmembrane domain and an intracellular domain common to the type 1 metabotropic glutamate receptor; and (ii) an extracellular domain which is shorter than type 1 metabotropic glutamate receptor by between 409 and 481 amino acid residues, with a substance which binds to said glutamate receptor protein; and (b) detecting inhibition or promotion of said reaction.

In a preferred embodiment, said glutamate receptor protein is prepared from a cell as disclosed herein, or a membrane fraction prepared from said cell.

In another aspect of the inventive subject matter, said detection of inhibition or promotion of said binding is by detecting a second messenger generated by the glutamate receptor protein.

Further, the inventive subject matter relates to a method for identifying an agonist for glutamic acid, comprising the steps of:

(a) reacting a glutamate receptor protein comprising:

(i) a transmembrane domain and an intracellular domain common to the type 1 metabotropic glutamate receptor; and (ii) an extracellular domain which is shorter than type 1 metabotropic glutamate receptor by between 409 and 481 amino acid residues, with a substance to be tested; and (b) detecting said reaction.

In another preferred embodiment, said glutamate receptor protein is prepared from a cell as disclosed herein, or a membrane fraction prepared from said cell.

In another aspect of the inventive subject matter, said method for detecting inhibition or promotion of said binding is by detecting a second messenger generated by the glutamate receptor protein.

The inventive subject matter additionally relates to an antibody which specifically binds to a glutamate receptor protein comprising:

(a) a transmembrane domain and an intracellular domain common to the type 1 metabotropic glutamate receptor; and (b) an extracellular domain which is shorter than type 1 metabotropic glutamate receptor by between 409 and 481 amino acid residues.

The inventive subject matter further relates to an active agent for modulating a second messenger which is generated by binding of glutamic acid to a glutamate receptor, produced by a process comprising the steps of:

(a) in the presence of a substance to be tested, reacting a glutamate receptor protein comprising:

(i) a transmembrane domain and an intracellular domain common to the type 1 metabotropic glutamate receptor; and (ii) an extracellular domain which is shorter than type 1 metabotropic glutamate receptor by between 409 and 481 amino acid residues, with a substance which binds to said protein;

(b) detecting inhibition or promotion of said reaction; and (c) analyzing said inhibition or promotion of said reaction by said substance to be tested, and determining whether said substance to be tested is an agonist, antagonist, or allosteric modulator for glutamic acid.

Further, the inventive subject matter relates to a pharmaceutical composition comprising:

(a) an active agent for modulating a second messenger which is generated by binding of glutamic acid to a glutamate receptor, produced by a process comprising the steps of:

(i) in the presence of a substance to be tested, reacting a glutamate receptor protein comprising:

(A) a transmembrane domain and an intracellular domain common to the type 1 metabotropic glutamate receptor, and (B) an extracellular domain which is shorter than type 1 metabotropic glutamate receptor by between 409 and 481 amino acid residues, with a substance which binds to said protein;

(ii) detecting inhibition or promotion of said reaction; and (iii) analyzing said inhibition or promotion of said reaction by said substance to be tested, and determining whether said substance to be tested is an agonist, antagonist, or allosteric modulator for glutamic acid; and (b) a pharmaceutically acceptable carrier.

The inventive subject matter also relates to an active agent for modulating a second messenger which is generated by binding of glutamic acid to a glutamate receptor, produced by a process comprising the steps of:

(a) in the presence of a substance to be tested, reacting a glutamate receptor protein comprising:

(i) a transmembrane domain and an intracellular domain common to the type 1 metabotropic glutamate receptor, and (ii) an extracellular domain which is shorter than type 1 metabotropic glutamate receptor by between 409 and 481 amino acid residues, with a substance which binds to said protein;

(b) detecting inhibition or promotion of said reaction; and (c) analyzing said inhibition or promotion of said reaction by said substance to be tested, and determining whether said substance to be tested is an agonist for glutamic acid.

Finally, the inventive subject matter relates to a pharmaceutical composition comprising:

(a) an active agent for modulating a second messenger which is generated by binding of glutamic acid to a glutamate receptor, produced by a process comprising the steps of:

(i) in the presence of a substance to be tested, reacting a glutamate receptor protein comprising:

(A) a transmembrane domain and an intracellular domain common to the type 1 metabotropic glutamate receptor, and (B) an extracellular domain which is shorter than type 1 metabotropic glutamate receptor by between 409 and 481 amino acid residues, with a substance which binds to said protein;

(ii) detecting inhibition or promotion of said reaction; and (iii) analyzing said inhibition or promotion of said reaction by said substance to be tested, and determining whether said substance to be tested is an agonist for glutamic acid; and (b) a pharmaceutically acceptable carrier.

Example 1

Cloning of Novel Metabotropic Glutamate Receptor cDNA from Circumvallate Papillae of Rat Total RNA derived from circumvallate papillae of ten rats of Wistar strain of 16 weeks age were extracted and subjected to a reverse transcription reaction to give cDNA (kit used: SuperScript, Gibco-BRL). cDNA coding for full length of mGluR1 was used as a template and a PCR was carried out by Z-Taq. This enzyme has a good replication efficiency at 3'-side and is suitable for a TOPO TA cloning reaction after that. The PCR product was subjected to electrophoresis using 2% agarose gel and the sequences were analyzed by an ABI Sequencer Model 3100 (ABI Co., Ltd.).

In six kinds of mGluR1 variant cDNA (mGluRTαa, mGluRTαb, mGluRTβa, mGluRTβb, mGluRTγa and mGluRTγb) found from circumvallate papillae, there are unique sequences at 5'-side, and in that areas, there are stop codons. The upstream side thereof is the same as that in the known substance, and that is quite similar to the sequence of mGluR1 of type A or type B. Such a unique part is not translated; therefore, all of the six kinds of mGluR1 variant cDNA are the same as a part of amino acid sequence of mGluR1; however, the chain length is short.

Forward primers specific to the six kinds of mGluR1 variant cDNA were prepared by Hokkaido System Science (the primers used are shown in Table 1) while, with regard to reverse primers, the followings were prepared from brain type mRNA sequence (Masu, et al., *Nature*, 349:760, 1991) (mGluR1-4253R 5'-TAC CAT ATG GAA TTG TGC TTT GTC A-3' (SEQ ID NO: 17) and mGluR1-4198R 5'-ATA ATT CAA GAG TCA CAA TCC TGG C-3' (SEQ ID NO: 18) for type A and mGluR1-3266R 5'-GGG TAT TGT CCT CTT CTT CCA CA-3' (SEQ ID NO: 19) for type B).

cDNA (150 ng) was used as a template, then 10 μM of forward and reverse primers, 10×LA PCR buffer, 2.5 mM of $MgCl_2$ and 2.5 mM of dNTP were mixed and 0.25 units of Z-Taq enzyme was placed therein to make the total volume 10 μl. Condition for the PCR was that GeneAmp PCR System 9700 was used where a cycle of 94° C.→20 seconds, 56° C.→1 minute and 68° C.→3 minutes was carried out for 30 cycles; finally, 10 minute extension→68° C. was done. Further, the second PCR was conducted and the resulting template was subjected to a cloning using pCRII-TOPO vector by a TOPO TA Cloning Kit (Invitrogen). Positive clones were subjected to a colony PCR while plasmids were purified by a Hispeed Plasmid Maxi-Kit (Quiagen) followed by subjecting to a functional analysis.

As a result, novel cDNAs mentioned in SEQ ID NOS: 1, 3, 5, 7, 9 and 10 were found. The resulting clones were found to be splicing variants of mGluR1 having novel extracellular domain.

TABLE 1

Primers

| Name | | Primer Name | SEQ ID NO | Sequence |
|---|---|---|---|---|
| Brain mGluR1a | PCR-1 | Forward mGluR1-50F | 20 | 5'-GAG ACC AAT AGC TGT GTC TAC CC-3' |
| | | Reverse mGluR1-4253R | 17 | 5'-TAC CAT ATG GAA TTG TGC TTT GTC A-3' |
| | PCR-2 | Forward mGluR1-114F | 21 | 5'-TGG ACA CCT GAT CCA CAC ACC TT-3' |
| | | Reverse mGluR1-4198R | 18 | 5'-ATA ATT CAA GAG TCA CAA TCC TGG C-3' |
| Brain mGluR1b | PCR-1 | Forward (same) | 20 | 5'-GAG ACC AAT AGC TGT GTC TAC CC-3' |
| | | Reverse (same) | 17 | 5'-TAC CAT ATG GAA TTG TGC TTT GTC A-3' |
| | PCR-2 | Forward (same) | 21 | 5'-TGG ACA CCT GAT CCA CAC ACC TT-3' |
| | | Reverse (same) | 18 | 5'-ATA ATT CAA GAG TCA CAA TCC TGG C-3' |
| mGluRTαa | PCR-1 | Forward mGluR1-718-2F | 11 | 5'-GTG AAT CAG AGG AAG TGT TCA GA-3' |
| | | Reverse mGluR1-4253R | 17 | 5'-TAC CAT ATG GAA TTG TGC TTT GTC A-3' |
| | PCR-2 | Forward mGluR1-718-3F | 12 | 5'-AAT GTA ACA GTC ACT GGT GCT GGG-3' |
| | | Reverse mGluR1-4198R | 18 | 5'-ATA ATT CAA GAG TCA CAA TCC TGG C-3' |
| mGluRTαb | PCR-1 | Forward mGluR1-718-2F | 11 | 5'-GTG AAT CAG AGG AAG TGT TCA GA-3' |
| | | Reverse mGluR1-3266R | 19 | 5'-GGG TAT TGT CCT CTT CTT CCA CA-3' |
| | PCR-2 | Forward mGluR1-718-3F | 12 | 5'-AAT GTA ACA GTC ACT GGT GCT GGG-3' |
| | | Reverse mGluR1-3266R | 19 | 5'-GGG TAT TGT CCT CTT CTT CCA CA-3' |
| mGluRTβa | PCR-1 | Forward mGluR1-790-1F | 13 | 5'-GGG ACT CTC TCC TGT CTT GTG AG-3' |
| | | Reverse mGluR1-4253R | 17 | 5'-TAC CAT ATG GAA TTG TGC TTT GTC A-3' |
| | PCR-2 | Forward mGluR1-790-2F | 14 | 5'-AGC ATA ACA GGG AAT TGC AGT GG-3' |
| | | Reverse mGluR1-4198R | 18 | 5'-ATA ATT CAA GAG TCA CAA TCC TGG C-3 |
| mGluRTβb | PCR-1 | Forward (same) | 13 | 5'-GGG ACT CTC TCC TGT CTT GTG AG-3' |
| | | Reverse (same) | 17 | 5'-TAC CAT ATG GAA TTG TGC TTT GTC A-3' |
| | PCR-2 | Forward (same) | 14 | 5'-AGC ATA ACA GGG AAT TGC AGT GG-3' |
| | | Reverse (same) | 18 | 5'-ATA ATT CAA GAG TCA CAA TCC TGG C-3 |
| mGluRTγa | PCR-1 | Forward mGluR1-1599-200F | 15 | 5'-CAG ACA GAA TAT AAT AGT CGG TC-3' |
| | | Reverse mGluR1-4253R | 17 | 5'-TAC CAT ATG GAA TTG TGC TTT GTC A-3' |
| | PCR-2 | Forward mGluR1-1599-221F | 16 | 5'-ACA AGT ACA AAA CAA GCT CTG C-3' |
| | | Reverse mGLuR1-4198R | 18 | 5'-ATA ATT CAA GAG TCA CAA TCC TGG-C3' |
| mGluRTγb | PCR-1 | Forward (same) | 15 | 5'-CAG ACA GAA TAT AAT AGT CGG TC-3' |
| | | Reverse (same) | 17 | 5'-TAC CAT ATG GAA TTG TGC TTT GTC A-3' |
| | PCR-2 | Forward (same) | 16 | 5'-ACA AGT ACA AAA CAA GCT CTG C-3' |
| | | Reverse (same) | 18 | 5'-ATA ATT CAA GAG TCA CAA TCC TGG-C3' |

Example 2

Identification of Localization of Glutamate Receptor by Immunostaining Means <1> Preparation of Slice Specimen of Tongue of Rat Under anesthetization with ether, right auricle of heart of rat (Wistar strain; male; 10 to 15 weeks age) was incised and blooded; immediately after that, tongue site was collected.

The cut-out tongue specimen was shaken for one night and day with 4% paraformaldehyde (4° C.) and immobilized by dipping therein. After that, it was dipped for 3 to 4 days in 20% sucrose-PBS to cryoprotect, embedded in Tissue-Tek$^R$ (OCT compound) and sliced into 5 to 7 μm using a cryostat. The slices were dried at room temperature and stored at 4° C. until subjecting to staining.

<2> Immunostaining by Anti-metabotropic Glutamate Receptor Type 1 Antibody

Immunostaining of the slices was carried out according to a method mentioned in Drengk, A. C., et al., *J. Auto. Nerv. Sys.*, 78:109–112, 2000 and Miampamba, M., et al., *J. Auto. Nerv. Sys.* 77:140–151, 1999. After the slices were washed with PBS firstly, they were treated with 3% hydrogen peroxide methanol in order to inhibit the reaction by intrinsic peroxidase. After that, the slices were washed with PBS and were subjected to a blocking for 1 hour using 1% normal bovine serum albumin-added PBS (1% BSA-PBS) containing 10% normal equine serum. After washing with PBS once again, they were made to react with a primary antibody (anti-mGluR1a, rabbit, polyclonal, Chemicon, cat# AB 1551) diluted with 1% BSA-PBS containing 1% normal equine serum at 4° C. for two nights. Then the slices were washed with PBS and made to react with the secondary antibody (anti-mGluR1a, rabbit, polyclonal, Chemicon, cat# AB 1551) diluted with 1% BSA-PBS at room temperature for one hour. Finally, reaction with ABC (avidin-biotin complex) was carried out using a Vectorstain Elite Kit (Vector) and colorized using 0.025% diaminobenzidine-0.25% nickel chloride-0.01% $H_2O_2$. After completion of the reaction, the slices were washed with PBS, dehydrated with ethanol-xylene, sealed and observed under a microscope. That which was not treated with a primary antibody was used as a negative control.

<3> Results

Figure 3A:
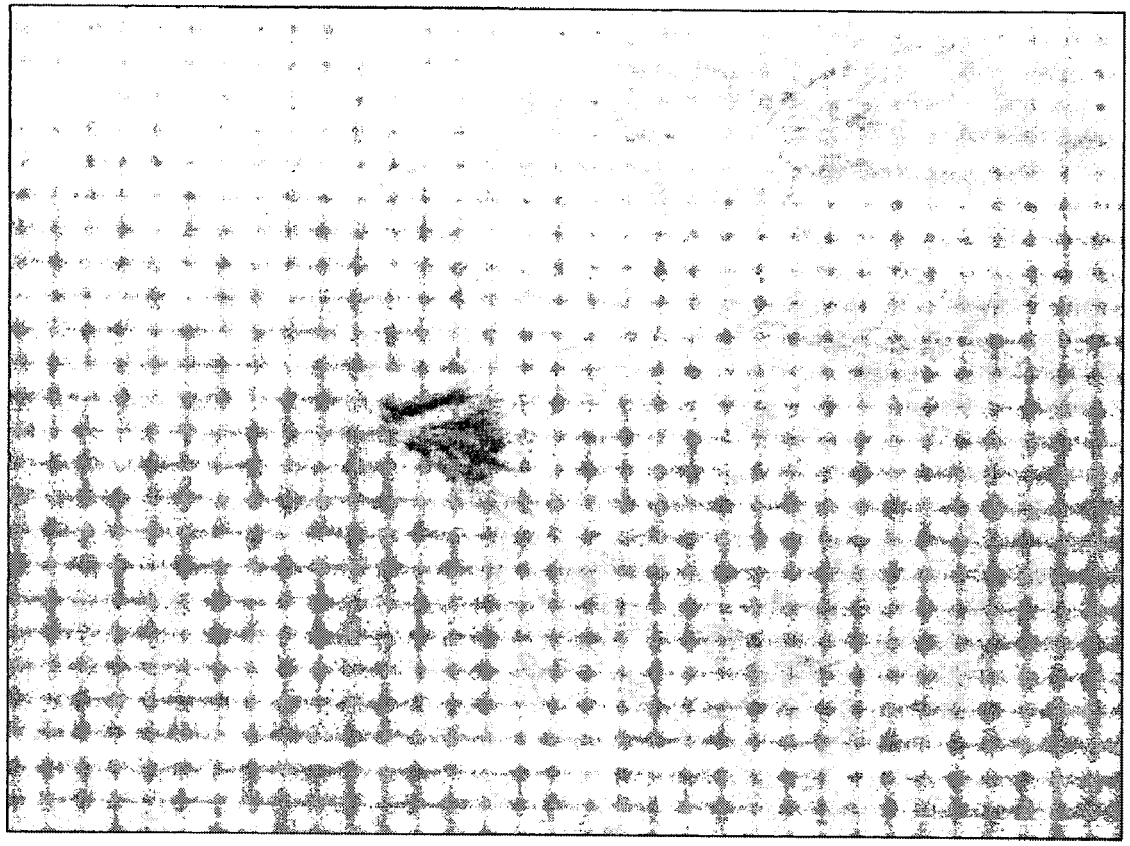
FIG. 3A is a photograph which shows the result of immunostaining of taste bud (circumvallate papilla) of rat by an anti-mGluR1 antibody.
Figure 3B:
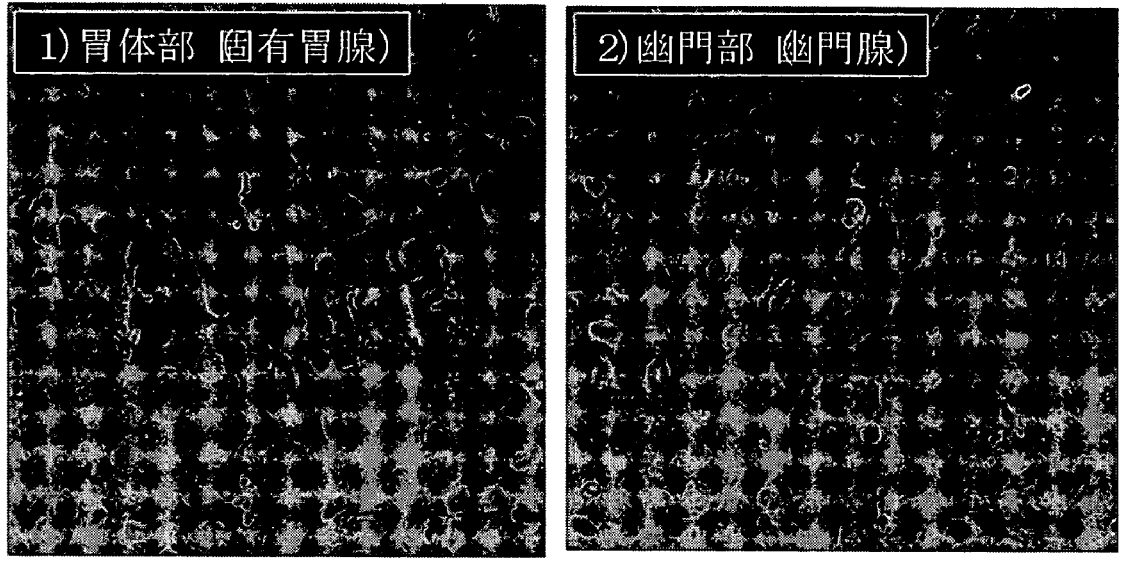
FIG. 3B is a photograph which shows the result of immunostaining of stomach of rat by an anti-mGluR1 antibody.

The result of the immunostaining is shown in FIG. 3. In the tongue specimen, taste cells were stained by the anti-mGluR1 antibody (FIG. 3A). It has been usually believed that no mGluR1 receptor is expressed in taste cells. Therefore, it is believed that mGluR1 variant is expressed in the taste cells; and functionally, relation to the umami reception was suggested. In the stomach specimens (FIG. 3B), each of cell which produces viscous liquid of pylorus and main cell and auxiliary cell of stomach body was stained by the anti-mGluR1. It has been generally believed no mGluR1 receptor is expressed in those cells. Therefore, mGluR1 variant was expressed in viscous liquid producing cell and main cell, and relation to secretion of viscous liquid and secretion of digestive enzyme was suggested, functionally.

Example 3

Presumption of Function of mGluR1 Variant

Rats (Wistar strain, males, 8 to 10 weeks age; Nippon Charles Liver) were fasted for 18 hours, laparotomy was conducted under anesthetization with urethane (1 g/kg; i.p.) and vagal gastric branch was exfoliated to an extent of about 5 mm. After vagal bundle was cut, it was placed on a small operation stand (8×6 mm), fat and bonded tissues around that were carefully detached and the terminal fiber at the side of organ was placed on a dipole electrode made of platinum for recording and insulated from the surrounding tissues by a mixture of liquid paraffin-vaseline (1:1). In the meanwhile, as a route for administration of MSG (sodium L-glutamate; manufactured by Ajinomoto Co., Inc.), a silicon tube for oral administration was implanted in the stomach.

Nerve action potential was amplified to an extent of 10,000-fold by a micropotential amplifier (DAM-80 manufactured by WPI); and after noise was reduced by a Vessel filter (4-pole, High Cut 10 Hz, Low Cut 1 KHz), it was subjected to an A/D conversion (Powerlab 4sp, manufactured by ADI Instruments, Inc.) and incorporated into a computer (sampling rate 3 KHz, iBook). At the same time, an amplified signal was separated by a window discriminator (DSE-435 manufactured by Daiya Medical Co., Ltd.) into a noise component and a nerve signal component together with monitoring by an oscilloscope, integrated for 5 seconds by a spike counter (DSE-335P manufactured by Daiya Medical Co., Ltd.) and recorded in a chart recorder (WT-465G manufactured by Nippon Koden Corporation). In analysis of the spike wave shape, a SHE software (manufactured by ADI Instruments, Inc.) was used.

Figure 4:
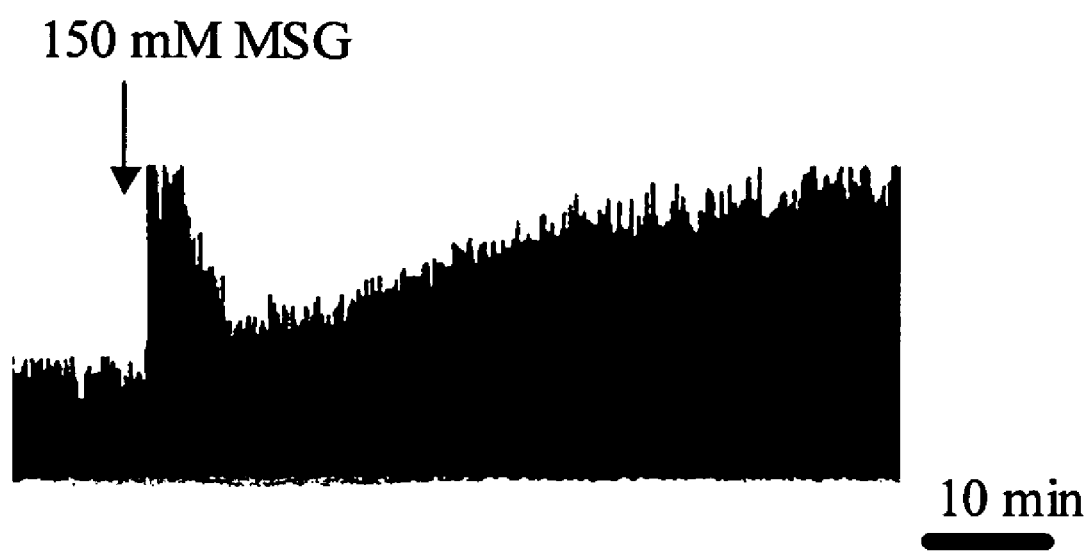
FIG. 4 is a drawing which shows the action of L-glutamic acid on vagal gastric branch-afferent nerve activity. The abscissa stands for time while the ordinate stands for nerve activity.

The result is shown in FIG. 4. Centripetal activity of vagal gastric branch upon administration of 150 mM of MSG to stomach was accelerated. Vagal centripetal path is believed to be a signal transmittance path which sends visceral sense, particularly nutrition information from stomach and intestine, to bulbar nucleus of solitary tract and conducts digestion adjustment by after-meal sense such as satisfactory and unpleasant senses and adjustment of vagal centrifugal path. Accordingly, the fact that vagal centripetal activity was accelerated by administration of MSG to digestive tracts shows the possibility that MSG is a cause for generation of its signal and that mGluR1 variant expressed in lumen of digestive tract mediates its signal generation.

Example 4

Expression of mGluR1 Variant in Tissues by RT-PCR Method

Figure 5A:
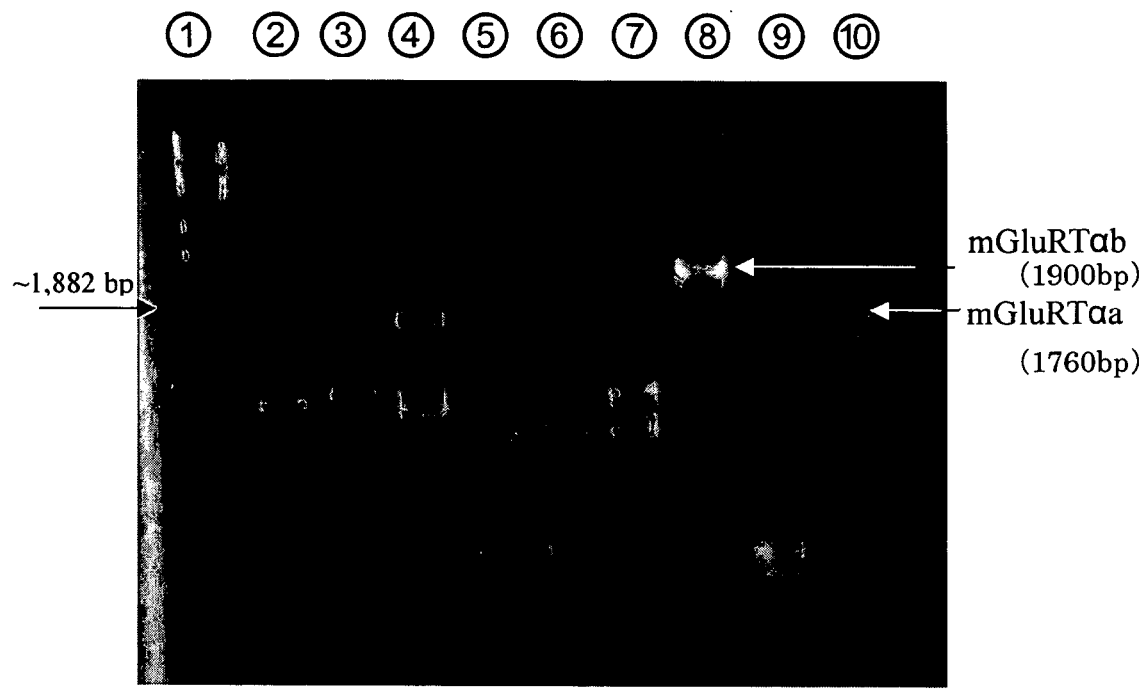
FIG. 5 is a drawing in which expression of nucleotide coding for mGluR1 variant by an RT-PCR method is confirmed (FIG. 5A: mGluRTα.
FIG. 5B: mGluRTβ). It has been confirmed that mGluR1 variant is expressed in taste bud.
Figure 5:
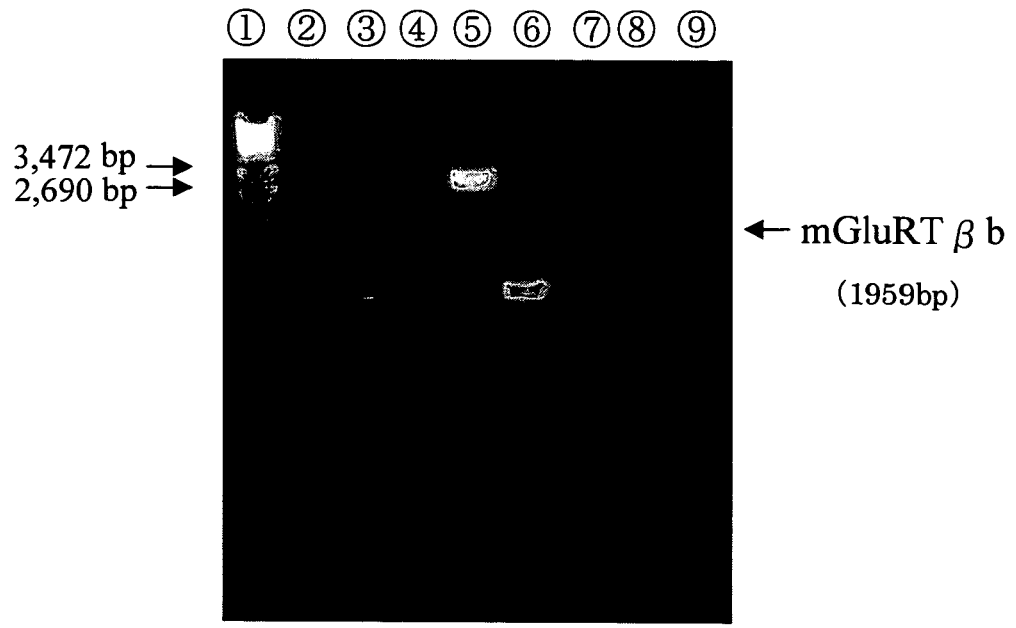

Whole Coding Sequence cDNA prepared by reverse transcription of total RNA of brain and circumvallate papilla with transcriptase was used. With regard to the 1st PCR primer, 30 cycles of PCR were carried out using mGluR1-790-1F (forward) (SEQ ID NO: 13), mGluR1-4253R (reverse) (SEQ ID NO: 17) and Z-Taq and the resulting PCR product diluted to an extent of 10-fold was used as a template for the 2nd PCR. For primer in the 2nd PCR, mGluR1-718-3F (forward; 5'-AAT GTA ACA GTC ACT GGT GCT GGG-3') (SEQ ID NO: 12) and mGluR1-3266R (reverse: 5'-GGG TAT TGT CCT CTT CTT CCA CA-3') (SEQ ID NO: 19) were used in the case of mGluRTα; while, in the case of mGluRTβ, mGluR1-790-2F (forward) (SEQ ID NO: 14) and mGluR1-4198R (reverse) (5'-ATA ATT CAA GAG TCA CAA TCC TGG C-3') were used. That was conducted in 30 cycles as well using Z-Taq. The resulting PCR products were already confirmed by an ABI Sequencer Model 3100. Incidentally, the type of the device used for the PCR was GeneAmp PCR System 9700. As a result, bands were confirmed near 1760 bp (type A) and 1900 bp (type B) for mGluRTα; while, for mGluRTβ, a band was confirmed near 2000 bp, and the expression was confirmed in circumvallate papilla (FIG. 5A and FIG. 5B).

Example 5

Analysis of Function: Oocyte Isolation

Oocyte-expressing strain of *Xenopus* was used for analysis of function of mGluR1 mRNA derived from circumvallate papilla of rats.

Female *Xenopus* (purchased from Watanabe Zoshoku) was bred in a fish tank until oocytes were isolated. The *Xenopus* was anesthetized with tricain methanesulfonate (MS 222, Sigma) dissolved in deionized water in a concentration of 1 g/L followed by buffering with $NaHCO_3$ (500 mg/L). Anatomy was conducted by hand and oocytes in stages V and VI were recovered from ovary and incubated (for 30 minutes to 1 hour) in a 0.2% collagenase S-1 (Nitta Gelatin) until dissociation took place. After treating with collagenase, the oocytes were washed; follicles were removed; selection was conducted under a microscope; and incubation was carried out at 18° C. for one night.

Metabotropic Glutamate cRNA Preparation

Variant mGluR1 cDNA was constructed by an RT-PCR method from total RNA of taste papilla and brain of rat using the following primers (mGluRTβ: 1st PCR: mGluR1-790-1F 5'-GGG ACT CTC TCC TGT CTT GTG AG-3' (SEQ ID NO: 13), mGluR1-4253R 5'-TAC CAT ATG GAA TTG TGC TTT GTC A-3' (SEQ ID NO: 17), 2nd PCR: mGluR1 790-2F forward 5'-AGC ATA ACA GGG AAT TGC AGT GG-3' (SEQ ID NO: 14), mGluR1 4198 reverse 5'-ATA ATT CAA GAG TCA CAA TCC TGG C-3' (SEQ ID NO: 18), mGluRTγ: 1st PCR: mGluR1-1599-200F 5'-CAG ACA GAA TAT AAT AGT CGG TC-3' (SEQ ID NO: 15), mGluR1-4253R 5'-TAC CAT ATG GAA TTG TGC TTT GTC A-3' (SEQ ID NO: 17), 2nd PCR: mGluR1-1599-221F 5'-ACA AGT ACA AAA CAA GCT CTG C-3' (SEQ ID NO: 16), mGluR1 4198 reverse 5'-ATA ATT CAA GAG TCA CAA TCC TGG C-3' (SEQ ID NO: 18)) and constitutive enzyme Z-Taq DNA polymerase. Since the polymerase remains blunt end in PCR fragments, PCR-amplified mGluRTβa and mGluRTγa template DNA were inserted into pCRII-TOPO vector (Invitrogen) by a TOPO-TA cloning reaction. pCRII-TOPO/mGluRTγ vector and pCRII-TOPO/mGluRTβ vector were made into straight lines using EcoRV and XbaI, respectively, extracted with a mixture of phenol and chloroform and precipitated with ethanol together with sodium acetate. After a sequence analysis, cRNA was prepared using a transcription kit for Sp6 promoter made by Ambion (mMESSAGE mMACHINE kit) binding to pCRII-TOPO promoter. Briefly, transcription of straight-chain template DNA of about 1 μg was carried out using 2 μL of enzyme mixture (the final concentration was made 20 μL volume using 10 μL of 2XNTP/Cap and 10× reaction buffer). For the synthesis of cRNA, the reaction solution was incubated at 37° C. for 3 hours and the residual template was decomposed by addition of 1 μL of DNase 1 for 15 minutes. The transcribed product was purified by extracting with phenol-chloroform and precipitating with isopropanol. cRNA was reconstructed in water treated with diethylpyrocarboxylic acid; and before injecting into oocytes, quantitative determination was conducted under irradiation with UV.

Microinjection of cRNA

After 24 hours from the recovery, 100 ng of mRNA per 25 nL of glass capillary tube having a standard diameter of 12 μm (Microinjector, WPI) was injected into oocytes of healthy *Xenopus* having transparent animal pole and vegetal pole. Incubation was carried out for 72 hours in an MBS solution [88 mM NaCl, 1 mM KCl, 2.4 mM $NaHCO_3$, 10 mM HEPES, 0.82 mM $MgSO_4$, 0.33 mM $Ca(NO_3)_2$ and 0.91 mM $CaCl_2$; pH 7.5] to which 2 mM pyruvic acid and 0.5 mM theophylline were added; and after that, the oocytes were used for an electrophysiological assay (Sanna, et al., 1994).

Method for Measurement of Membrane Current

Membrane current of oocytes was measured by a two-electrode membrane potential fixation method using Geneclamp Amplifier (Axon Instruments). Glass microelectrode used for the measurement was prepared by a puller (Shutter Co., Ltd.) and that where electrode resistance upon filling with 3M KCl was 1 to 3 MΩ was used. The treated oocytes were transferred to a chamber for the measurement; glass electrode was inserted under a stereoscopic microscope; and under fixation of potential to −70 mV, calcium-dependent chloride current upon stimulation with glutamic acid was measured. The experiment was carried out for both of the cases of cells which express mGluR1 variant of rat and which do not.

Figure 6:
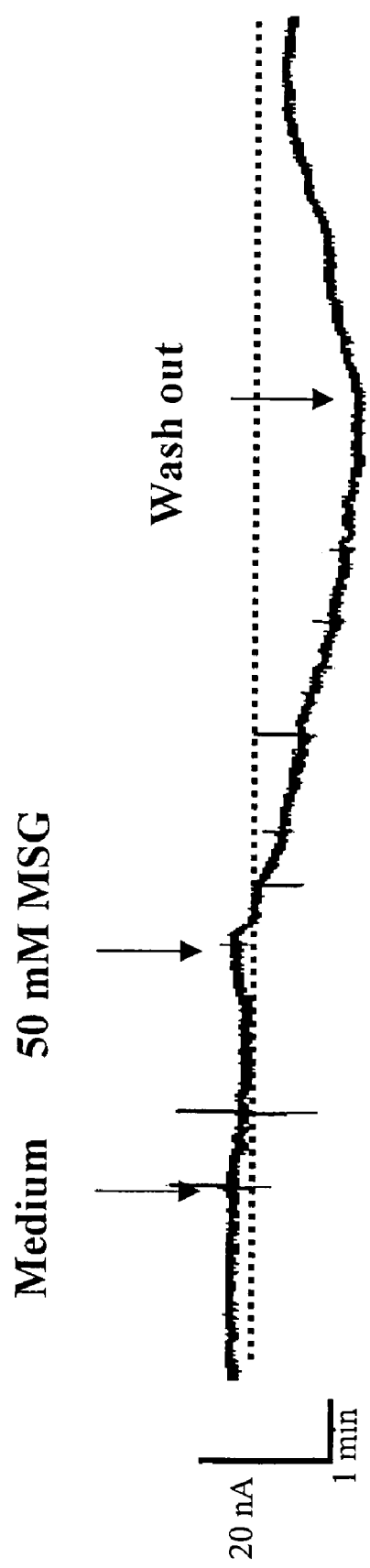
FIG. 6 is a drawing which shows changes in membrane currency when mGluR1 variant is expressed in oocytes of *Xenopus* and sodium glutamate is acted thereon.

The result of record of measurement of membrane current of oocytes where mGluRTβa was expressed is shown in FIG. 6. When the medium in an inner area of the measuring bath was substituted with a medium containing 50 mM of sodium glutamate (MSG), continuous introvert current was induced and the introvert current was confirmed to disappear by performing substitution of the medium again. That is believed to be due to the fact that glutamic acid acted on the receptor whereupon a calcium-dependent chloride channel via an intracellular information transmittance system was activated; and as a result, that was measured as introvert current. The same introvert current was also observed in mGluRTγa-expressing oocytes. Incidentally, although not shown here, such a reaction was not observed in oocytes into which cRNA was not injected. Therefore, it has now been proved that the mGluR1 variant which is a cloning gene product of the present invention has an action of conducting the glutamic acid reception and inducing an intracellular calcium mobilization. According to the same proceeding, it has been also confirmed that mGluRTα has a ligand action and it is also possible to search agonist, antagonist or allosteric modulator.

INDUSTRIAL APPLICABILITY

In accordance with the present invention, there is provided a novel metabotropic glutamate receptor. This glutamate receptor is able to be used for the search of agonist, antagonist or allosteric modulator for glutamic acid. It is also able to be used as a food additive as a novel umami-tasting substance and also as a drug for improving diseases and symptoms caused by metabolism abnormality in digestive tracts.

The invention being thus described, it will be obvious that the same may be modified or varied in many ways. Such modifications and variations are not to be regarded as a departure from the spirit and scope of the invention and all such modifications and variations are intended to be included within the scope of the following claims.

We claim:

1. An isolated DNA molecule that codes for a glutamate receptor protein consisting of an amino acid sequence represented by a member selected from the group consisting of amino acids 1–790 of SEQ ID NO: 6, amino acids 73–790 of SEQ ID NO: 6, amino acids 1–497 of SEQ ID NO: 8, and amino acids 73–497 of SEQ ID NO: 8.

2. The isolated DNA molecule of claim 1, comprising:
   a nucleic acid sequence represented by a member selected from the group consisting of SEQ ID NO: 1, SEQ ID NO: 3, SEQ ID NO: 5, SEQ ID NO: 7, SEQ ID NO: 9 and SEQ ID NO: 10; or
   a nucleic acid sequence that hybridizes at 60° and at a salt concentration corresponding to 0.1×SSC, 0.1% SDS to a complement of the nucleic acid sequence represented by a member selected from the group consisting of SEQ ID NO: 1, SEQ ID NO: 3, SEQ ID NO: 5, SEQ ID NO: 7, SEQ ID NO: 9, and SEQ ID NO: 10, and wherein said isolated DNA molecule does not code for a brain-type metabolic glutamate receptor type 1.

3. The isolated DNA molecule of claim 1, wherein the isolated DNA molecule is represented by SEQ ID NO: 7.

4. A cell transformed with an isolated DNA molecule coding for the glutamate receptor protein according to claim 1 in an expressible form.

5. The cell of claim 4, wherein said isolated DNA molecule in an expressible form further comprises a vector.

6. A method for producing a glutamate receptor protein, comprising the steps of:
   (a) incubating a host cell transformed with DNA coding for a glutamate receptor protein according to claim 1, in an expressible form, in a medium wherein said glutamate receptor protein is expressed; and
   (b) collecting said expressed glutamate receptor protein from said host cells.

* * * * *

UNITED STATES PATENT AND TRADEMARK OFFICE
CERTIFICATE OF CORRECTION

| | | |
|---|---|---|
| PATENT NO. | : 7,186,819 B2 | Page 1 of 1 |
| APPLICATION NO. | : 10/918857 | |
| DATED | : March 6, 2007 | |
| INVENTOR(S) | : San Gabriel et al. | |

It is certified that error appears in the above-identified patent and that said Letters Patent is hereby corrected as shown below:

Column 59, Line 52, Please delete "60°" and replace with -- 60°C --

Signed and Sealed this

First Day of May, 2007

JON W. DUDAS
*Director of the United States Patent and Trademark Office*

SEQUENCE LISTING

<160> NUMBER OF SEQ ID NOS: 21

<210> SEQ ID NO 1
<211> LENGTH: 2714
<212> TYPE: DNA
<213> ORGANISM: Rattus norvegicus
<220> FEATURE:
<221> NAME/KEY: CDS
<222> LOCATION: (334)..(2490)
<223> OTHER INFORMATION:

<400> SEQUENCE: 1

```
ctgttacttg ttcaaagggt acttcatgct tttaaagagt tgatcaacta aatacataca      60
ttattacctt tgaagtata  aacagaaaaa tgttgagagc aataaatcat ttgacaaaag     120
tgaattgatc tagagacatt ctatgtgaat cagaggaagt gttcagaaca cactataaat     180
gtaacagtca ctggtgctgg gatgtgacga cgatccaagc tttgacctct tgtctctcac     240
taaaatccat ttacaagtta cctttgtttt ctctctcagg gaaatatccg gtgagactca     300
cctgtatttg ttttctatgt taggtatgac att atg aat ctg cag tac aca gaa     354
                                   Met Asn Leu Gln Tyr Thr Glu
                                     1               5
```

```
gct aat cgc tat gac tat gtc cac gtg ggg acc tgg cat gaa gga gtg       402
Ala Asn Arg Tyr Asp Tyr Val His Val Gly Thr Trp His Glu Gly Val
        10                  15                  20 ctg aat att gat gat tac aaa atc cag atg aac aaa agc gga atg gta       450
Leu Asn Ile Asp Asp Tyr Lys Ile Gln Met Asn Lys Ser Gly Met Val
 25                  30                  35 cga tct gtg tgc agt gag cct tgc tta aag ggt cag att aag gtc ata       498
Arg Ser Val Cys Ser Glu Pro Cys Leu Lys Gly Gln Ile Lys Val Ile
40                  45                  50                  55 cgg aaa gga gaa gtg agc tgc tgc tgg atc tgc acg gcc tgc aaa gag       546
Arg Lys Gly Glu Val Ser Cys Cys Trp Ile Cys Thr Ala Cys Lys Glu
                    60                  65                  70 aat gag ttt gtg cag gac gag ttc acc tgc aga gcc tgt gac ctg ggg       594
Asn Glu Phe Val Gln Asp Glu Phe Thr Cys Arg Ala Cys Asp Leu Gly
        75                  80                  85 tgg tgg ccc aac gca gag ctc aca ggc tgt gag ccc att cct gtc cgt       642
Trp Trp Pro Asn Ala Glu Leu Thr Gly Cys Glu Pro Ile Pro Val Arg
     90                  95                 100 tat ctt gag tgg agt gac ata gaa tct atc ata gcc atc gcc ttt tct       690
Tyr Leu Glu Trp Ser Asp Ile Glu Ser Ile Ile Ala Ile Ala Phe Ser
105                 110                 115 tgc ctg ggc atc ctc gtg acg ctg ttt gtc acc ctc atc ttc gtt ctg       738
Cys Leu Gly Ile Leu Val Thr Leu Phe Val Thr Leu Ile Phe Val Leu
120                 125                 130                 135 tac cgg gac aca ccc gtg gtc aaa tcc tcc agt agg gag ctc tgc tat       786
Tyr Arg Asp Thr Pro Val Val Lys Ser Ser Ser Arg Glu Leu Cys Tyr
                140                 145                 150 atc att ctg gct ggt att ttc ctc ggc tat gtg tgc cct ttc acc ctc       834
Ile Ile Leu Ala Gly Ile Phe Leu Gly Tyr Val Cys Pro Phe Thr Leu
        155                 160                 165 atc gcc aaa cct act acc aca tcc tgc tac ctc cag cgc ctc cta gtt       882
Ile Ala Lys Pro Thr Thr Thr Ser Cys Tyr Leu Gln Arg Leu Leu Val
    170                 175                 180 ggc ctc tct tct gcc atg tgc tac tct gct tta gtg acc aaa acc aat       930
Gly Leu Ser Ser Ala Met Cys Tyr Ser Ala Leu Val Thr Lys Thr Asn
185                 190                 195 cgt att gca cgc atc ctg gct ggc agc aag aag aag atc tgc acc cgg       978
```

```
                                                         -continued

Arg Ile Ala Arg Ile Leu Ala Gly Ser Lys Lys Lys Ile Cys Thr Arg
200                 205                 210                 215 aag ccc aga ttc atg agc gct tgg gcc caa gtg atc ata gcc tcc att      1026
Lys Pro Arg Phe Met Ser Ala Trp Ala Gln Val Ile Ile Ala Ser Ile
                220                 225                 230 ctg att agt gta cag cta aca cta gtg gtg acc ttg atc atc atg gag      1074
Leu Ile Ser Val Gln Leu Thr Leu Val Val Thr Leu Ile Ile Met Glu
                235                 240                 245 cct ccc atg ccc att ttg tcc tac ccg agt atc aag gaa gtc tac ctt      1122
Pro Pro Met Pro Ile Leu Ser Tyr Pro Ser Ile Lys Glu Val Tyr Leu
            250                 255                 260 atc tgc aat acc agc aac ctg ggt gta gtg gcc cct gtg ggt tac aat      1170
Ile Cys Asn Thr Ser Asn Leu Gly Val Val Ala Pro Val Gly Tyr Asn
            265                 270                 275 gga ctc ctc atc atg agc tgt acc tac tat gcc ttc aag acc cgc aac      1218
Gly Leu Leu Ile Met Ser Cys Thr Tyr Tyr Ala Phe Lys Thr Arg Asn
280                 285                 290                 295 gtg ccg gcc aac ttc aat gag gct aaa tac atc gcc ttc acc atg tac      1266
Val Pro Ala Asn Phe Asn Glu Ala Lys Tyr Ile Ala Phe Thr Met Tyr
                300                 305                 310 act acc tgc atc atc tgg ctg gct ttc gtt ccc att tac ttt ggg agc      1314
Thr Thr Cys Ile Ile Trp Leu Ala Phe Val Pro Ile Tyr Phe Gly Ser
                315                 320                 325 aac tac aag atc atc act acc tgc ttc gcg gtg agc ctc agt gtg acg      1362
Asn Tyr Lys Ile Ile Thr Thr Cys Phe Ala Val Ser Leu Ser Val Thr
                330                 335                 340 gtg gcc ctg ggg tgc atg ttt act ccg aag atg tac atc atc att gcc      1410
Val Ala Leu Gly Cys Met Phe Thr Pro Lys Met Tyr Ile Ile Ile Ala
345                 350                 355 aaa cct gag agg aac gtc cgc agt gcc ttc acg acc tct gat gtt gtc      1458
Lys Pro Glu Arg Asn Val Arg Ser Ala Phe Thr Thr Ser Asp Val Val
360                 365                 370                 375 cgc atg cac gtc ggt gat ggc aaa ctg ccg tgc cgc tcc aac acc ttc      1506
Arg Met His Val Gly Asp Gly Lys Leu Pro Cys Arg Ser Asn Thr Phe
                380                 385                 390 ctc aac att ttc cgg aga aag aag ccc ggg gca ggg aat gcc aat tct      1554
Leu Asn Ile Phe Arg Arg Lys Lys Pro Gly Ala Gly Asn Ala Asn Ser
                395                 400                 405 aac ggc aag tct gtg tca tgg tct gaa cca ggt gga aga cag gcg ccc      1602
Asn Gly Lys Ser Val Ser Trp Ser Glu Pro Gly Gly Arg Gln Ala Pro
            410                 415                 420 aag gga cag cac gtg tgg cag cgc ctc tct gtg cac gtg aag acc aac      1650
Lys Gly Gln His Val Trp Gln Arg Leu Ser Val His Val Lys Thr Asn
425                 430                 435 gag acg gcc tgt aac caa aca gcc gta atc aaa ccc ctc act aaa agt      1698
Glu Thr Ala Cys Asn Gln Thr Ala Val Ile Lys Pro Leu Thr Lys Ser
440                 445                 450                 455 tac caa ggc tct ggc aag agc ctg acc ttt tca gat gcc agc acc aag      1746
Tyr Gln Gly Ser Gly Lys Ser Leu Thr Phe Ser Asp Ala Ser Thr Lys
            460                 465                 470 acc ctt tac aat gtg gaa gaa gag gac aat acc cct tct gct cac ttc      1794
Thr Leu Tyr Asn Val Glu Glu Glu Asp Asn Thr Pro Ser Ala His Phe
                475                 480                 485 agc cct ccc agc agc cct tct atg gtg gtg cac cga cgc ggg cca ccc      1842
Ser Pro Pro Ser Ser Pro Ser Met Val Val His Arg Arg Gly Pro Pro
            490                 495                 500 gtg gcc acc aca cca cct ctg cca ccc cat ctg acc gca gaa gag acc      1890
Val Ala Thr Thr Pro Pro Leu Pro Pro His Leu Thr Ala Glu Glu Thr
505                 510                 515
```

-continued

| | | | | | | | | | | | | | | | |
|---|---|---|---|---|---|---|---|---|---|---|---|---|---|---|---|
| ccc | ctg | ttc | ctg | gct | gat | tcc | gtc | atc | ccc | aag | ggc | ttg | cct | cct | cct | 1938 |
| Pro | Leu | Phe | Leu | Ala | Asp | Ser | Val | Ile | Pro | Lys | Gly | Leu | Pro | Pro | Pro | |
| 520 | | | | | 525 | | | | | 530 | | | | | 535 | |

```
ccc ctg ttc ctg gct gat tcc gtc atc ccc aag ggc ttg cct cct cct    1938
Pro Leu Phe Leu Ala Asp Ser Val Ile Pro Lys Gly Leu Pro Pro Pro
520                 525                 530                 535 ctc ccg cag cag cag cca cag cag ccg ccc cct cag cag ccc ccg cag    1986
Leu Pro Gln Gln Gln Pro Gln Gln Pro Pro Pro Gln Gln Pro Pro Gln
        540                 545                 550 cag ccc aag tcc ctg atg gac cag ctg caa ggc gta gtc acc aac ttc    2034
Gln Pro Lys Ser Leu Met Asp Gln Leu Gln Gly Val Val Thr Asn Phe
        555                 560                 565 ggt tcg ggg att cca gat ttc cat gcg gtg ctg gca ggc ccg ggg aca    2082
Gly Ser Gly Ile Pro Asp Phe His Ala Val Leu Ala Gly Pro Gly Thr
        570                 575                 580 cca gga aac agc ctg cgc tct ctg tac ccg ccc ccg cct ccg ccg caa    2130
Pro Gly Asn Ser Leu Arg Ser Leu Tyr Pro Pro Pro Pro Pro Pro Gln
    585                 590                 595 cac ctg cag atg ctg ccc ctg cac ctg agc acc ttc cag gag gag tcc    2178
His Leu Gln Met Leu Pro Leu His Leu Ser Thr Phe Gln Glu Glu Ser
600                 605                 610                 615 atc tcc cct cct ggg gag gac atc gat gat gac agt gag aga ttc aag    2226
Ile Ser Pro Pro Gly Glu Asp Ile Asp Asp Asp Ser Glu Arg Phe Lys
                620                 625                 630 ctc ctg cag gag ttc gtg tac gag cgc gaa ggg aac acc gaa gaa gat    2274
Leu Leu Gln Glu Phe Val Tyr Glu Arg Glu Gly Asn Thr Glu Glu Asp
            635                 640                 645 gaa ttg gaa gag gag gag gac ctg ccc aca gcc agc aag ctg acc cct    2322
Glu Leu Glu Glu Glu Glu Asp Leu Pro Thr Ala Ser Lys Leu Thr Pro
        650                 655                 660 gag gat tct cct gcc ctg acg cct cct tct cct ttc cga gat tcc gtg    2370
Glu Asp Ser Pro Ala Leu Thr Pro Pro Ser Pro Phe Arg Asp Ser Val
665                 670                 675 gcc tct ggc agc tca gtg ccc agt tcc ccc gta tct gag tcg gtc ctc    2418
Ala Ser Gly Ser Ser Val Pro Ser Ser Pro Val Ser Glu Ser Val Leu
680                 685                 690                 695 tgc acc cct cca aat gta acc tac gcc tct gtc att ctg agg gac tac    2466
Cys Thr Pro Pro Asn Val Thr Tyr Ala Ser Val Ile Leu Arg Asp Tyr
                700                 705                 710 aag caa agc tct tcc acc ctg tag tgtgtgtgtg tgtgtggggg cgggggagt    2520
Lys Gln Ser Ser Ser Thr Leu
            715 gcgcatggag aagccagaga tgccaaggag tgtcaaccct tccagaaatg tgtagaaagc   2580 agggtgaggg atggggatgg aggaccacgg tctgcaggga agaaaaaaaa aatgctgcgg   2640 ctgccttaaa gaaggagagg gacgatgcca actgaacagt ggtcctggcc aggattgtga   2700 ctcttgaatt attc                                                    2714

<210> SEQ ID NO 2
<211> LENGTH: 718
<212> TYPE: PRT
<213> ORGANISM: Rattus norvegicus

<400> SEQUENCE: 2

Met Asn Leu Gln Tyr Thr Glu Ala Asn Arg Tyr Asp Tyr Val His Val
1               5                   10                  15

Gly Thr Trp His Glu Gly Val Leu Asn Ile Asp Asp Tyr Lys Ile Gln
            20                  25                  30

Met Asn Lys Ser Gly Met Val Arg Ser Val Cys Ser Glu Pro Cys Leu
        35                  40                  45

Lys Gly Gln Ile Lys Val Ile Arg Lys Gly Glu Val Ser Cys Cys Trp
    50                  55                  60
```

-continued

```
Ile Cys Thr Ala Cys Lys Glu Asn Glu Phe Val Gln Asp Glu Phe Thr
 65                  70                  75                  80

Cys Arg Ala Cys Asp Leu Gly Trp Trp Pro Asn Ala Glu Leu Thr Gly
                 85                  90                  95

Cys Glu Pro Ile Pro Val Arg Tyr Leu Glu Trp Ser Asp Ile Glu Ser
            100                 105                 110

Ile Ile Ala Ile Ala Phe Ser Cys Leu Gly Ile Leu Val Thr Leu Phe
        115                 120                 125

Val Thr Leu Ile Phe Val Leu Tyr Arg Asp Thr Pro Val Val Lys Ser
    130                 135                 140

Ser Ser Arg Glu Leu Cys Tyr Ile Ile Leu Ala Gly Ile Phe Leu Gly
145                 150                 155                 160

Tyr Val Cys Pro Phe Thr Leu Ile Ala Lys Pro Thr Thr Thr Ser Cys
                165                 170                 175

Tyr Leu Gln Arg Leu Leu Val Gly Leu Ser Ser Ala Met Cys Tyr Ser
            180                 185                 190

Ala Leu Val Thr Lys Thr Asn Arg Ile Ala Arg Ile Leu Ala Gly Ser
        195                 200                 205

Lys Lys Lys Ile Cys Thr Arg Lys Pro Arg Phe Met Ser Ala Trp Ala
210                 215                 220

Gln Val Ile Ile Ala Ser Ile Leu Ile Ser Val Gln Leu Thr Leu Val
225                 230                 235                 240

Val Thr Leu Ile Ile Met Glu Pro Pro Met Pro Ile Leu Ser Tyr Pro
                245                 250                 255

Ser Ile Lys Glu Val Tyr Leu Ile Cys Asn Thr Ser Asn Leu Gly Val
            260                 265                 270

Val Ala Pro Val Gly Tyr Asn Gly Leu Leu Ile Met Ser Cys Thr Tyr
        275                 280                 285

Tyr Ala Phe Lys Thr Arg Asn Val Pro Ala Asn Phe Asn Glu Ala Lys
    290                 295                 300

Tyr Ile Ala Phe Thr Met Tyr Thr Thr Cys Ile Ile Trp Leu Ala Phe
305                 310                 315                 320

Val Pro Ile Tyr Phe Gly Ser Asn Tyr Lys Ile Ile Thr Thr Cys Phe
                325                 330                 335

Ala Val Ser Leu Ser Val Thr Val Ala Leu Gly Cys Met Phe Thr Pro
            340                 345                 350

Lys Met Tyr Ile Ile Ile Ala Lys Pro Glu Arg Asn Val Arg Ser Ala
        355                 360                 365

Phe Thr Thr Ser Asp Val Val Arg Met His Val Gly Asp Gly Lys Leu
    370                 375                 380

Pro Cys Arg Ser Asn Thr Phe Leu Asn Ile Phe Arg Arg Lys Lys Pro
385                 390                 395                 400

Gly Ala Gly Asn Ala Asn Ser Asn Gly Lys Ser Val Ser Trp Ser Glu
                405                 410                 415

Pro Gly Gly Arg Gln Ala Pro Lys Gly Gln His Val Trp Gln Arg Leu
            420                 425                 430

Ser Val His Val Lys Thr Asn Glu Thr Ala Cys Asn Gln Thr Ala Val
        435                 440                 445

Ile Lys Pro Leu Thr Lys Ser Tyr Gln Gly Ser Gly Lys Ser Leu Thr
    450                 455                 460

Phe Ser Asp Ala Ser Thr Lys Thr Leu Tyr Asn Val Glu Glu Glu Asp
465                 470                 475                 480
```

```
Asn Thr Pro Ser Ala His Phe Ser Pro Pro Ser Ser Pro Ser Met Val
                485                 490                 495

Val His Arg Arg Gly Pro Pro Val Ala Thr Thr Pro Pro Leu Pro Pro
            500                 505                 510

His Leu Thr Ala Glu Glu Thr Pro Leu Phe Leu Ala Asp Ser Val Ile
            515                 520                 525

Pro Lys Gly Leu Pro Pro Pro Leu Pro Gln Gln Gln Pro Gln Gln Pro
            530                 535                 540

Pro Pro Gln Gln Pro Gln Gln Pro Lys Ser Leu Met Asp Gln Leu
545                 550                 555                 560

Gln Gly Val Val Thr Asn Phe Gly Ser Gly Ile Pro Asp Phe His Ala
                565                 570                 575

Val Leu Ala Gly Pro Gly Thr Pro Gly Asn Ser Leu Arg Ser Leu Tyr
            580                 585                 590

Pro Pro Pro Pro Pro Gln His Leu Gln Met Leu Pro Leu His Leu
            595                 600                 605

Ser Thr Phe Gln Glu Glu Ser Ile Ser Pro Pro Gly Glu Asp Ile Asp
    610                 615                 620

Asp Asp Ser Glu Arg Phe Lys Leu Leu Gln Glu Phe Val Tyr Glu Arg
625                 630                 635                 640

Glu Gly Asn Thr Glu Glu Asp Glu Leu Glu Glu Glu Asp Leu Pro
                645                 650                 655

Thr Ala Ser Lys Leu Thr Pro Glu Asp Ser Pro Ala Leu Thr Pro Pro
                660                 665                 670

Ser Pro Phe Arg Asp Ser Val Ala Ser Gly Ser Ser Val Pro Ser Ser
            675                 680                 685

Pro Val Ser Glu Ser Val Leu Cys Thr Pro Pro Asn Val Thr Tyr Ala
            690                 695                 700

Ser Val Ile Leu Arg Asp Tyr Lys Gln Ser Ser Ser Thr Leu
705                 710                 715

<210> SEQ ID NO 3
<211> LENGTH: 1635
<212> TYPE: DNA
<213> ORGANISM: Rattus norvegicus
<220> FEATURE:
<221> NAME/KEY: CDS
<222> LOCATION: (334)..(1611)
<223> OTHER INFORMATION:

<400> SEQUENCE: 3
ctgttacttg ttcaaagggt acttcatgct tttaaagagt tgatcaacta aatacataca      60
ttattacctt tgaagtata aacagaaaaa tgttgagagc aataaatcat ttgacaaaag     120
tgaattgatc tagagacatt ctatgtgaat cagaggaagt gttcagaaca cactataaat     180
gtaacagtca ctggtgctgg gatgtgacga cgatccaagc tttgacctct tgtctctcac     240
taaaatccat ttacaagtta cctttgtttt ctctctcagg gaaatatccg gtgagactca     300
cctgtatttg ttttctatgt taggtatgac att atg aat ctg cag tac aca gaa    354
                                    Met Asn Leu Gln Tyr Thr Glu
                                     1               5 gct aat cgc tat gac tat gtc cac gtg ggg acc tgg cat gaa gga gtg    402
Ala Asn Arg Tyr Asp Tyr Val His Val Gly Thr Trp His Glu Gly Val
         10                  15                  20 ctg aat att gat gat tac aaa atc cag atg aac aaa agc gga atg gta    450
Leu Asn Ile Asp Asp Tyr Lys Ile Gln Met Asn Lys Ser Gly Met Val
     25                  30                  35
```

-continued

| | |
|---|---|
| cga tct gtg tgc agt gag cct tgc tta aag ggt cag att aag gtc ata<br>Arg Ser Val Cys Ser Glu Pro Cys Leu Lys Gly Gln Ile Lys Val Ile<br>40                       45                       50                     55 | 498 |
| cgg aaa gga gaa gtg agc tgc tgc tgg atc tgc acg gcc tgc aaa gag<br>Arg Lys Gly Glu Val Ser Cys Cys Trp Ile Cys Thr Ala Cys Lys Glu<br>                    60                       65                      70 | 546 |
| aat gag ttt gtg cag gac gag ttc acc tgc aga gcc tgt gac ctg ggg<br>Asn Glu Phe Val Gln Asp Glu Phe Thr Cys Arg Ala Cys Asp Leu Gly<br>             75                       80                       85 | 594 |
| tgg tgg ccc aac gca gag ctc aca ggc tgt gag ccc att cct gtc cgt<br>Trp Trp Pro Asn Ala Glu Leu Thr Gly Cys Glu Pro Ile Pro Val Arg<br>           90                       95                    100 | 642 |
| tat ctt gag tgg agt gac ata gaa tct ata gcc atc gcc ttt tct<br>Tyr Leu Glu Trp Ser Asp Ile Glu Ser Ile Ile Ala Ile Ala Phe Ser<br>105                    110                   115 | 690 |
| tgc ctg ggc atc ctc gtg acg ctg ttt gtc acc ctc atc ttc gtt ctg<br>Cys Leu Gly Ile Leu Val Thr Leu Phe Val Thr Leu Ile Phe Val Leu<br>120                    125                   130                  135 | 738 |
| tac cgg gac aca ccc gtg gtc aaa tcc tcc agt agg gag ctc tgc tat<br>Tyr Arg Asp Thr Pro Val Val Lys Ser Ser Ser Arg Glu Leu Cys Tyr<br>                    140                   145                   150 | 786 |
| atc att ctg gct ggt att ttc ctc ggc tat gtg tgc cct ttc acc ctc<br>Ile Ile Leu Ala Gly Ile Phe Leu Gly Tyr Val Cys Pro Phe Thr Leu<br>155                    160                   165 | 834 |
| atc gcc aaa cct act acc aca tcc tgc tac ctc cag cgc ctc cta gtt<br>Ile Ala Lys Pro Thr Thr Thr Ser Cys Tyr Leu Gln Arg Leu Leu Val<br>170                    175                   180 | 882 |
| ggc ctc tct tct gcc atg tgc tac tct gct tta gtg acc aaa acc aat<br>Gly Leu Ser Ser Ala Met Cys Tyr Ser Ala Leu Val Thr Lys Thr Asn<br>185                    190                   195 | 930 |
| cgt att gca cgc atc ctg gct ggc agc aag aag aag atc tgc acc cgg<br>Arg Ile Ala Arg Ile Leu Ala Gly Ser Lys Lys Lys Ile Cys Thr Arg<br>200                    205                   210                  215 | 978 |
| aag ccc aga ttc atg agc gct tgg gcc caa gtg atc ata gcc tcc att<br>Lys Pro Arg Phe Met Ser Ala Trp Ala Gln Val Ile Ile Ala Ser Ile<br>                    220                   225                   230 | 1026 |
| ctg att agt gta cag cta aca cta gtg gtg acc ttg atc atc atg gag<br>Leu Ile Ser Val Gln Leu Thr Leu Val Val Thr Leu Ile Ile Met Glu<br>235                    240                   245 | 1074 |
| cct ccc atg ccc att ttg tcc tac ccg agt atc aag gaa gtc tac ctt<br>Pro Pro Met Pro Ile Leu Ser Tyr Pro Ser Ile Lys Glu Val Tyr Leu<br>250                    255                   260 | 1122 |
| atc tgc aat acc agc aac ctg ggt gta gtg gcc cct gtg ggt tac aat<br>Ile Cys Asn Thr Ser Asn Leu Gly Val Val Ala Pro Val Gly Tyr Asn<br>265                    270                   275 | 1170 |
| gga ctc ctc atc atg agc tgt acc tac tat gcc ttc aag acc cgc aac<br>Gly Leu Leu Ile Met Ser Cys Thr Tyr Tyr Ala Phe Lys Thr Arg Asn<br>280                    285                   290                  295 | 1218 |
| gtg ccg gcc aac ttc aat gag gct aaa tac atc gcc ttc acc atg tac<br>Val Pro Ala Asn Phe Asn Glu Ala Lys Tyr Ile Ala Phe Thr Met Tyr<br>                    300                   305                   310 | 1266 |
| act acc tgc atc atc tgg ctg gct ttc gtt ccc att tac ttt ggg agc<br>Thr Thr Cys Ile Ile Trp Leu Ala Phe Val Pro Ile Tyr Phe Gly Ser<br>315                    320                   325 | 1314 |
| aac tac aag atc atc act acc tgc ttc gcg gtg agc ctc agt gtg acg<br>Asn Tyr Lys Ile Ile Thr Thr Cys Phe Ala Val Ser Leu Ser Val Thr<br>330                    335                   340 | 1362 |
| gtg gcc ctg ggg tgc atg ttt act ccg aag atg tac atc atc att gcc<br>Val Ala Leu Gly Cys Met Phe Thr Pro Lys Met Tyr Ile Ile Ile Ala<br>345                    350                   355 | 1410 |

```
aaa cct gag agg aac gtc cgc agt gcc ttc acg acc tct gat gtt gtc    1458
Lys Pro Glu Arg Asn Val Arg Ser Ala Phe Thr Thr Ser Asp Val Val
360                 365                 370                 375 cgc atg cac gtc ggt gat ggc aaa ctg ccg tgc cgc tcc aac acc ttc    1506
Arg Met His Val Gly Asp Gly Lys Leu Pro Cys Arg Ser Asn Thr Phe
                380                 385                 390 ctc aac att ttc cgg aga aag aag ccc ggg gca ggg aat gcc aag aag    1554
Leu Asn Ile Phe Arg Arg Lys Lys Pro Gly Ala Gly Asn Ala Lys Lys
            395                 400                 405 agg cag cca gaa ttc tcg ccc agc agc cag tgt ccg tcg gca cat gcg    1602
Arg Gln Pro Glu Phe Ser Pro Ser Ser Gln Cys Pro Ser Ala His Ala
410                 415                 420 cag ctt tga aaaccccac actgcagtga atgt                               1635
Gln Leu
    425

<210> SEQ ID NO 4
<211> LENGTH: 425
<212> TYPE: PRT
<213> ORGANISM: Rattus norvegicus

<400> SEQUENCE: 4

Met Asn Leu Gln Tyr Thr Glu Ala Asn Arg Tyr Asp Tyr Val His Val
1               5                   10                  15

Gly Thr Trp His Glu Gly Val Leu Asn Ile Asp Asp Tyr Lys Ile Gln
                20                  25                  30

Met Asn Lys Ser Gly Met Val Arg Ser Val Cys Ser Glu Pro Cys Leu
            35                  40                  45

Lys Gly Gln Ile Lys Val Ile Arg Lys Gly Glu Val Ser Cys Cys Trp
    50                  55                  60

Ile Cys Thr Ala Cys Lys Glu Asn Glu Phe Val Gln Asp Glu Phe Thr
65                  70                  75                  80

Cys Arg Ala Cys Asp Leu Gly Trp Trp Pro Asn Ala Glu Leu Thr Gly
                85                  90                  95

Cys Glu Pro Ile Pro Val Arg Tyr Leu Glu Trp Ser Asp Ile Glu Ser
            100                 105                 110

Ile Ile Ala Ile Ala Phe Ser Cys Leu Gly Ile Leu Val Thr Leu Phe
        115                 120                 125

Val Thr Leu Ile Phe Val Leu Tyr Arg Asp Thr Pro Val Val Lys Ser
130                 135                 140

Ser Ser Arg Glu Leu Cys Tyr Ile Ile Leu Ala Gly Ile Phe Leu Gly
145                 150                 155                 160

Tyr Val Cys Pro Phe Thr Leu Ile Ala Lys Pro Thr Thr Thr Ser Cys
                165                 170                 175

Tyr Leu Gln Arg Leu Leu Val Gly Leu Ser Ser Ala Met Cys Tyr Ser
            180                 185                 190

Ala Leu Val Thr Lys Thr Asn Arg Ile Ala Arg Ile Leu Ala Gly Ser
        195                 200                 205

Lys Lys Lys Ile Cys Thr Arg Lys Pro Arg Phe Met Ser Ala Trp Ala
    210                 215                 220

Gln Val Ile Ile Ala Ser Ile Leu Ile Ser Val Gln Leu Thr Leu Val
225                 230                 235                 240

Val Thr Leu Ile Ile Met Glu Pro Pro Met Pro Ile Leu Ser Tyr Pro
                245                 250                 255

Ser Ile Lys Glu Val Tyr Leu Ile Cys Asn Thr Ser Asn Leu Gly Val
            260                 265                 270
```

-continued

```
Val Ala Pro Val Gly Tyr Asn Gly Leu Leu Ile Met Ser Cys Thr Tyr
            275                 280                 285
Tyr Ala Phe Lys Thr Arg Asn Val Pro Ala Asn Phe Asn Glu Ala Lys
            290                 295                 300
Tyr Ile Ala Phe Thr Met Tyr Thr Thr Cys Ile Ile Trp Leu Ala Phe
305                 310                 315                 320
Val Pro Ile Tyr Phe Gly Ser Asn Tyr Lys Ile Ile Thr Thr Cys Phe
                325                 330                 335
Ala Val Ser Leu Ser Val Thr Val Ala Leu Gly Cys Met Phe Thr Pro
            340                 345                 350
Lys Met Tyr Ile Ile Ile Ala Lys Pro Glu Arg Asn Val Arg Ser Ala
            355                 360                 365
Phe Thr Thr Ser Asp Val Val Arg Met His Val Gly Asp Gly Lys Leu
370                 375                 380
Pro Cys Arg Ser Asn Thr Phe Leu Asn Ile Phe Arg Arg Lys Lys Pro
385                 390                 395                 400
Gly Ala Gly Asn Ala Lys Lys Arg Gln Pro Glu Phe Ser Pro Ser Ser
                405                 410                 415
Gln Cys Pro Ser Ala His Ala Gln Leu
            420                 425

<210> SEQ ID NO 5
<211> LENGTH: 3038
<212> TYPE: DNA
<213> ORGANISM: Rattus norvegicus
<220> FEATURE:
<221> NAME/KEY: CDS
<222> LOCATION: (442)..(2814)
<223> OTHER INFORMATION:

<400> SEQUENCE: 5
gggactctct cctgtcttgt gaggctgaag cataacaggg aattgcagtg gcttaaagta     60
gactttggct tctctggatt gctttgttta tagatatctc tgaactcatt tgtgagacac    120
tgtcttcttc ttctctcttc accccaaccc ctgcattgtt ttagtgatgg atgggcagac    180
agagatgaag tcatcgaagg ctatgaggtg aagccaacg gagggatcac aataaagctt     240
cagtctccag aggtcaggtc atttgatgac tacttcctga agctgaggct ggacaccaac    300
acaaggaatc cttggttccc tgagttctgg caacatcgct tccagtgtcg cctacctgga    360
cacctcttgg aaaaccccaa ctttaagaaa gtgtgcacag gaaatgaaag cttggaagaa    420
aactatgtcc aggacagcaa a atg gga ttt gtc atc aat gcc atc tat gcc     471
                       Met Gly Phe Val Ile Asn Ala Ile Tyr Ala
                        1               5                  10 atg gca cat ggg ctg cag aac atg cac cat gct ctg tgt ccc ggc cat     519
Met Ala His Gly Leu Gln Asn Met His His Ala Leu Cys Pro Gly His
                15                  20                  25 gtg ggc ctg tgt gat gct atg aaa ccc att gat ggc agg aag ctc ctg     567
Val Gly Leu Cys Asp Ala Met Lys Pro Ile Asp Gly Arg Lys Leu Leu
            30                  35                  40 gat ttc ctc atc aaa tcc tct ttt gtc gga gtg tct gga gag gag gtg     615
Asp Phe Leu Ile Lys Ser Ser Phe Val Gly Val Ser Gly Glu Glu Val
        45                  50                  55 tgg ttc gat gag aag ggg gat gct ccc gga agg tat gac att atg aat     663
Trp Phe Asp Glu Lys Gly Asp Ala Pro Gly Arg Tyr Asp Ile Met Asn
    60                  65                  70 ctg cag tac aca gaa gct aat cgc tat gac tat gtc cac gtg ggg acc     711
Leu Gln Tyr Thr Glu Ala Asn Arg Tyr Asp Tyr Val His Val Gly Thr
```

-continued

```
             75                  80                  85                  90
tgg cat gaa gga gtg ctg aat att gat gat tac aaa atc cag atg aac        759
Trp His Glu Gly Val Leu Asn Ile Asp Asp Tyr Lys Ile Gln Met Asn
                    95                 100                 105 aaa agc gga atg gta cga tct gtg tgc agt gag cct tgc tta aag ggt        807
Lys Ser Gly Met Val Arg Ser Val Cys Ser Glu Pro Cys Leu Lys Gly
                110                 115                 120 cag att aag gtc ata cgg aaa gga gaa gtg agc tgc tgc tgg atc tgc        855
Gln Ile Lys Val Ile Arg Lys Gly Glu Val Ser Cys Cys Trp Ile Cys
                125                 130                 135 acg gcc tgc aaa gag aat gag ttt gtg cag gac gag ttc acc tgc aga        903
Thr Ala Cys Lys Glu Asn Glu Phe Val Gln Asp Glu Phe Thr Cys Arg
                140                 145                 150 gcc tgt gac ctg ggg tgg tgg ccc aac gca gag ctc aca ggc tgt gag        951
Ala Cys Asp Leu Gly Trp Trp Pro Asn Ala Glu Leu Thr Gly Cys Glu
155                 160                 165                 170 ccc att cct gtc cgt tat ctt gag tgg agt gac ata gaa tct atc ata        999
Pro Ile Pro Val Arg Tyr Leu Glu Trp Ser Asp Ile Glu Ser Ile Ile
                175                 180                 185 gcc atc gcc ttt tct tgc ctg ggc atc ctc gtg acg ctg ttt gtc acc       1047
Ala Ile Ala Phe Ser Cys Leu Gly Ile Leu Val Thr Leu Phe Val Thr
                190                 195                 200 ctc atc ttc gtt ctg tac cgg gac aca ccc gtg gtc aaa tcc tcc agt       1095
Leu Ile Phe Val Leu Tyr Arg Asp Thr Pro Val Val Lys Ser Ser Ser
                205                 210                 215 agg gag ctc tgc tat atc att ctg gct ggt att ttc ctc ggc tat gtg       1143
Arg Glu Leu Cys Tyr Ile Ile Leu Ala Gly Ile Phe Leu Gly Tyr Val
220                 225                 230 tgc cct ttc acc ctc atc gcc aaa cct act acc aca tcc tgc tac ctc       1191
Cys Pro Phe Thr Leu Ile Ala Lys Pro Thr Thr Thr Ser Cys Tyr Leu
235                 240                 245                 250 cag cgc ctc cta gtt ggc ctc tct tct gcc atg tgc tac tct gct tta       1239
Gln Arg Leu Leu Val Gly Leu Ser Ser Ala Met Cys Tyr Ser Ala Leu
                255                 260                 265 gtg acc aaa acc aat cgt att gca cgc atc ctg gct ggc agc aag aag       1287
Val Thr Lys Thr Asn Arg Ile Ala Arg Ile Leu Ala Gly Ser Lys Lys
                270                 275                 280 aag atc tgc acc cgg aag ccc aga ttc atg agc gct tgg gcc caa gtg       1335
Lys Ile Cys Thr Arg Lys Pro Arg Phe Met Ser Ala Trp Ala Gln Val
                285                 290                 295 ata ata gcc tcc att ctg att agt gta cag cta aca cta gtg gtg acc       1383
Ile Ile Ala Ser Ile Leu Ile Ser Val Gln Leu Thr Leu Val Val Thr
                300                 305                 310 ttg atc atc atg gag cct ccc atg ccc att ttg tcc tac ccg agt atc       1431
Leu Ile Ile Met Glu Pro Pro Met Pro Ile Leu Ser Tyr Pro Ser Ile
315                 320                 325                 330 aag gaa gtc tac ctt atc tgc aat acc agc aac ctg ggt gta gtg gcc       1479
Lys Glu Val Tyr Leu Ile Cys Asn Thr Ser Asn Leu Gly Val Val Ala
                335                 340                 345 cct gtg ggt tac aat gga ctc ctc atc atg agc tgt acc tac tat gcc       1527
Pro Val Gly Tyr Asn Gly Leu Leu Ile Met Ser Cys Thr Tyr Tyr Ala
                350                 355                 360 ttc aag acc cgc aac gtg ccg gcc aac ttc aat gag gct aaa tac atc       1575
Phe Lys Thr Arg Asn Val Pro Ala Asn Phe Asn Glu Ala Lys Tyr Ile
                365                 370                 375 gcc ttc acc atg tac act acc tgc atc atc tgg ctg gct ttc gtt ccc       1623
Ala Phe Thr Met Tyr Thr Thr Cys Ile Ile Trp Leu Ala Phe Val Pro
                380                 385                 390 att tac ttt ggg agc aac tac aag atc atc act acc tgc ttc gcg gtg       1671
Ile Tyr Phe Gly Ser Asn Tyr Lys Ile Ile Thr Thr Cys Phe Ala Val
```

```
Ile Tyr Phe Gly Ser Asn Tyr Lys Ile Ile Thr Thr Cys Phe Ala Val
395                 400                 405                 410 agc ctc agt gtg acg gtg gcc ctg ggg tgc atg ttt act ccg aag atg       1719
Ser Leu Ser Val Thr Val Ala Leu Gly Cys Met Phe Thr Pro Lys Met
                415                 420                 425 tac atc atc att gcc aaa cct gag agg aac gtc cgc agt gcc ttc acg       1767
Tyr Ile Ile Ile Ala Lys Pro Glu Arg Asn Val Arg Ser Ala Phe Thr
            430                 435                 440 acc tct gat gtt gtc cgc atg cac gtc ggt gat ggc aaa ctg ccg tgc       1815
Thr Ser Asp Val Val Arg Met His Val Gly Asp Gly Lys Leu Pro Cys
                445                 450                 455 cgc tcc aac acc ttc ctc aac att ttc cgg aga aag aag ccc ggg gca       1863
Arg Ser Asn Thr Phe Leu Asn Ile Phe Arg Arg Lys Lys Pro Gly Ala
            460                 465                 470 ggg aat gcc aat tct aac ggc aag tct gtg tca tgg tct gaa cca ggt       1911
Gly Asn Ala Asn Ser Asn Gly Lys Ser Val Ser Trp Ser Glu Pro Gly
475                 480                 485                 490 gga aga cag gcg ccc aag gga cag cac gtg tgg cag cgc ctc tct gtg       1959
Gly Arg Gln Ala Pro Lys Gly Gln His Val Trp Gln Arg Leu Ser Val
                495                 500                 505 cac gtg aag acc aac gag acg gcc tgt aac caa aca gcc gta atc aaa       2007
His Val Lys Thr Asn Glu Thr Ala Cys Asn Gln Thr Ala Val Ile Lys
            510                 515                 520 ccc ctc act aaa agt tac caa ggc tct ggc aag agc ctg acc ttt tca       2055
Pro Leu Thr Lys Ser Tyr Gln Gly Ser Gly Lys Ser Leu Thr Phe Ser
                525                 530                 535 gat gcc agc acc aag acc ctt tac aat gtg gaa gaa gag gac aat acc       2103
Asp Ala Ser Thr Lys Thr Leu Tyr Asn Val Glu Glu Glu Asp Asn Thr
540                 545                 550 cct tct gct cac ttc agc cct ccc agc agc cct tct atg gtg gtg cac       2151
Pro Ser Ala His Phe Ser Pro Pro Ser Ser Pro Ser Met Val Val His
555                 560                 565                 570 cga cgc ggg cca ccc gtg gcc acc aca cca cct ctg cca ccc cat ctg       2199
Arg Arg Gly Pro Pro Val Ala Thr Thr Pro Pro Leu Pro Pro His Leu
                575                 580                 585 acc gca gaa gag acc ccc ctg ttc ctg gct gat tcc gtc atc ccc aag       2247
Thr Ala Glu Glu Thr Pro Leu Phe Leu Ala Asp Ser Val Ile Pro Lys
            590                 595                 600 ggc ttg cct cct cct ctc ccg cag cag cag cca cag cag ccg ccc cct       2295
Gly Leu Pro Pro Pro Leu Pro Gln Gln Gln Pro Gln Gln Pro Pro Pro
                605                 610                 615 cag cag ccc ccg cag cag ccc aag tcc ctg atg gac cag ctg caa ggc       2343
Gln Gln Pro Pro Gln Gln Pro Lys Ser Leu Met Asp Gln Leu Gln Gly
620                 625                 630 gta gtc acc aac ttc ggt tcg ggg att cca gat ttc cat gcg gtg ctg       2391
Val Val Thr Asn Phe Gly Ser Gly Ile Pro Asp Phe His Ala Val Leu
635                 640                 645                 650 gca ggc ccg ggg aca cca gga aac agc ctg cgc tct ctg tac ccg ccc       2439
Ala Gly Pro Gly Thr Pro Gly Asn Ser Leu Arg Ser Leu Tyr Pro Pro
                655                 660                 665 ccg cct ccg ccg caa cac ctg cag atg ctg ccc ctg cac ctg agc acc       2487
Pro Pro Pro Pro Gln His Leu Gln Met Leu Pro Leu His Leu Ser Thr
                670                 675                 680 ttc cag gag gag tcc atc tcc cct cct ggg gag gac atc gat gat gac       2535
Phe Gln Glu Glu Ser Ile Ser Pro Pro Gly Glu Asp Ile Asp Asp Asp
            685                 690                 695 agt gag aga ttc aag ctc ctg cag gag ttc gtg tac gag cgc gaa ggg       2583
Ser Glu Arg Phe Lys Leu Leu Gln Glu Phe Val Tyr Glu Arg Glu Gly
700                 705                 710
```

| | | | | | | | | | | | | | | | |
|---|---|---|---|---|---|---|---|---|---|---|---|---|---|---|---|
| aac | acc | gaa | gaa | gat | gaa | ttg | gaa | gag | gag | gag | gac | ctg | ccc | aca | gcc | 2631 |
| Asn | Thr | Glu | Glu | Asp | Glu | Leu | Glu | Glu | Glu | Glu | Asp | Leu | Pro | Thr | Ala |
| 715 | | | | 720 | | | | | 725 | | | | | 730 |

```
aac acc gaa gaa gat gaa ttg gaa gag gag gag gac ctg ccc aca gcc    2631
Asn Thr Glu Glu Asp Glu Leu Glu Glu Glu Glu Asp Leu Pro Thr Ala
715                 720                 725                 730 agc aag ctg acc cct gag gat tct cct gcc ctg acg cct cct tct cct    2679
Ser Lys Leu Thr Pro Glu Asp Ser Pro Ala Leu Thr Pro Pro Ser Pro
            735                 740                 745 ttc cga gat tcc gtg gcc tct ggc agc tca gtg ccc agt tcc ccc gta    2727
Phe Arg Asp Ser Val Ala Ser Gly Ser Ser Val Pro Ser Ser Pro Val
                750                 755                 760 tct gag tcg gtc ctc tgc acc cct cca aat gta acc tac gcc tct gtc    2775
Ser Glu Ser Val Leu Cys Thr Pro Pro Asn Val Thr Tyr Ala Ser Val
        765                 770                 775 att ctg agg gac tac aag caa agc tct tcc acc ctg tag tgtgtgtgtg     2824
Ile Leu Arg Asp Tyr Lys Gln Ser Ser Ser Thr Leu
            780                 785                 790 tgtgtggggg cggggggagt gcgcatggag aagccagaga tgccaaggag tgtcaaccct   2884
tccagaaatg tgtagaaagc agggtgaggg atggggatgg aggaccacgg tctgcaggga   2944
agaaaaaaaa aatgctgcgg ctgccttaaa gaaggagagg gacgatgcca actgaacagt   3004
ggtcctggcc aggattgtga ctcttgaatt attc                               3038
```

<210> SEQ ID NO 6
<211> LENGTH: 790
<212> TYPE: PRT
<213> ORGANISM: Rattus norvegicus

<400> SEQUENCE: 6

```
Met Gly Phe Val Ile Asn Ala Ile Tyr Ala Met Ala His Gly Leu Gln
1               5                   10                  15

Asn Met His His Ala Leu Cys Pro Gly His Val Gly Leu Cys Asp Ala
            20                  25                  30

Met Lys Pro Ile Asp Gly Arg Lys Leu Leu Asp Phe Leu Ile Lys Ser
        35                  40                  45

Ser Phe Val Gly Val Ser Gly Glu Glu Val Trp Phe Asp Glu Lys Gly
    50                  55                  60

Asp Ala Pro Gly Arg Tyr Asp Ile Met Asn Leu Gln Tyr Thr Glu Ala
65                  70                  75                  80

Asn Arg Tyr Asp Tyr Val His Val Gly Thr Trp His Glu Gly Val Leu
                85                  90                  95

Asn Ile Asp Asp Tyr Lys Ile Gln Met Asn Lys Ser Gly Met Val Arg
            100                 105                 110

Ser Val Cys Ser Glu Pro Cys Leu Lys Gly Gln Ile Lys Val Ile Arg
        115                 120                 125

Lys Gly Glu Val Ser Cys Cys Trp Ile Cys Thr Ala Cys Lys Glu Asn
    130                 135                 140

Glu Phe Val Gln Asp Glu Phe Thr Cys Arg Ala Cys Asp Leu Gly Trp
145                 150                 155                 160

Trp Pro Asn Ala Glu Leu Thr Gly Cys Glu Pro Ile Pro Val Arg Tyr
                165                 170                 175

Leu Glu Trp Ser Asp Ile Glu Ser Ile Ala Ile Ala Phe Ser Cys
            180                 185                 190

Leu Gly Ile Leu Val Thr Leu Phe Val Thr Leu Ile Phe Val Leu Tyr
        195                 200                 205

Arg Asp Thr Pro Val Val Lys Ser Ser Ser Arg Glu Leu Cys Tyr Ile
    210                 215                 220

Ile Leu Ala Gly Ile Phe Leu Gly Tyr Val Cys Pro Phe Thr Leu Ile
```

-continued

```
            225                 230                 235                 240
    Ala Lys Pro Thr Thr Thr Ser Cys Tyr Leu Gln Arg Leu Leu Val Gly
                        245                 250                 255

Leu Ser Ser Ala Met Cys Tyr Ser Ala Leu Val Thr Lys Thr Asn Arg
                    260                 265                 270

Ile Ala Arg Ile Leu Ala Gly Ser Lys Lys Ile Cys Thr Arg Lys
                275                 280                 285

Pro Arg Phe Met Ser Ala Trp Ala Gln Val Ile Ile Ala Ser Ile Leu
            290                 295                 300

Ile Ser Val Gln Leu Thr Leu Val Val Thr Leu Ile Ile Met Glu Pro
    305                 310                 315                 320

Pro Met Pro Ile Leu Ser Tyr Pro Ser Ile Lys Glu Val Tyr Leu Ile
                        325                 330                 335

Cys Asn Thr Ser Asn Leu Gly Val Val Ala Pro Val Gly Tyr Asn Gly
                    340                 345                 350

Leu Leu Ile Met Ser Cys Thr Tyr Tyr Ala Phe Lys Thr Arg Asn Val
                355                 360                 365

Pro Ala Asn Phe Asn Glu Ala Lys Tyr Ile Ala Phe Thr Met Tyr Thr
            370                 375                 380

Thr Cys Ile Ile Trp Leu Ala Phe Val Pro Ile Tyr Phe Gly Ser Asn
    385                 390                 395                 400

Tyr Lys Ile Ile Thr Thr Cys Phe Ala Val Ser Leu Ser Val Thr Val
                        405                 410                 415

Ala Leu Gly Cys Met Phe Thr Pro Lys Met Tyr Ile Ile Ile Ala Lys
                    420                 425                 430

Pro Glu Arg Asn Val Arg Ser Ala Phe Thr Thr Ser Asp Val Val Arg
                435                 440                 445

Met His Val Gly Asp Gly Lys Leu Pro Cys Arg Ser Asn Thr Phe Leu
            450                 455                 460

Asn Ile Phe Arg Arg Lys Pro Gly Ala Gly Asn Ala Asn Ser Asn
    465                 470                 475                 480

Gly Lys Ser Val Ser Trp Ser Glu Pro Gly Gly Arg Gln Ala Pro Lys
                        485                 490                 495

Gly Gln His Val Trp Gln Arg Leu Ser Val His Val Lys Thr Asn Glu
                    500                 505                 510

Thr Ala Cys Asn Gln Thr Ala Val Ile Lys Pro Leu Thr Lys Ser Tyr
                515                 520                 525

Gln Gly Ser Gly Lys Ser Leu Thr Phe Ser Asp Ala Ser Thr Lys Thr
            530                 535                 540

Leu Tyr Asn Val Glu Glu Glu Asp Asn Thr Pro Ser Ala His Phe Ser
    545                 550                 555                 560

Pro Pro Ser Ser Pro Ser Met Val Val His Arg Arg Gly Pro Pro Val
                        565                 570                 575

Ala Thr Thr Pro Pro Leu Pro Pro His Leu Thr Ala Glu Glu Thr Pro
                    580                 585                 590

Leu Phe Leu Ala Asp Ser Val Ile Pro Lys Gly Leu Pro Pro Pro Leu
                595                 600                 605

Pro Gln Gln Gln Pro Gln Gln Pro Pro Gln Gln Pro Pro Gln Gln
            610                 615                 620

Pro Lys Ser Leu Met Asp Gln Leu Gln Gly Val Val Thr Asn Phe Gly
    625                 630                 635                 640

Ser Gly Ile Pro Asp Phe His Ala Val Leu Ala Gly Pro Gly Thr Pro
                        645                 650                 655
```

```
Gly Asn Ser Leu Arg Ser Leu Tyr Pro Pro Pro Pro Gln His
            660                 665             670

Leu Gln Met Leu Pro Leu His Leu Ser Thr Phe Gln Glu Glu Ser Ile
        675                 680             685

Ser Pro Pro Gly Glu Asp Ile Asp Asp Ser Glu Arg Phe Lys Leu
        690             695             700

Leu Gln Glu Phe Val Tyr Glu Arg Glu Gly Asn Thr Glu Glu Asp Glu
705                 710             715                 720

Leu Glu Glu Glu Asp Leu Pro Thr Ala Ser Lys Leu Thr Pro Glu
                725             730             735

Asp Ser Pro Ala Leu Thr Pro Pro Ser Pro Phe Arg Asp Ser Val Ala
            740             745             750

Ser Gly Ser Ser Val Pro Ser Pro Val Ser Glu Ser Val Leu Cys
        755             760             765

Thr Pro Pro Asn Val Thr Tyr Ala Ser Val Ile Leu Arg Asp Tyr Lys
        770             775             780

Gln Ser Ser Ser Thr Leu
785             790

<210> SEQ ID NO 7
<211> LENGTH: 1959
<212> TYPE: DNA
<213> ORGANISM: Rattus norvegicus
<220> FEATURE:
<221> NAME/KEY: CDS
<222> LOCATION: (442)..(1935)
<223> OTHER INFORMATION:

<400> SEQUENCE: 7
gggactctct cctgtcttgt gaggctgaag cataacaggg aattgcagtg gcttaaagta      60
gactttggct tctctggatt gctttgttta tagatatctc tgaactcatt tgtgagacac     120
tgtcttcttc ttctctcttc accccaaccc ctgcattgtt ttagtgatgg atgggcagac     180
agagatgaag tcatcgaagg ctatgaggtg gaagccaacg gagggatcac aataaagctt     240
cagtctccag aggtcaggtc atttgatgac tacttcctga agctgaggct ggacaccaac     300
acaaggaatc cttggttccc tgagttctgg caacatcgct tccagtgtcg cctacctgga     360
cacctcttgg aaaaccccaa ctttaagaaa gtgtgcacag gaaatgaaag cttggaagaa     420
aactatgtcc aggacagcaa a atg gga ttt gtc atc aat gcc atc tat gcc      471
                        Met Gly Phe Val Ile Asn Ala Ile Tyr Ala
                          1               5                  10 atg gca cat ggg ctg cag aac atg cac cat gct ctg tgt ccc ggc cat     519
Met Ala His Gly Leu Gln Asn Met His His Ala Leu Cys Pro Gly His
                 15                  20                  25 gtg ggc ctg tgt gat gct atg aaa ccc att gat ggc agg aag ctc ctg     567
Val Gly Leu Cys Asp Ala Met Lys Pro Ile Asp Gly Arg Lys Leu Leu
             30                  35                  40 gat ttc ctc atc aaa tcc tct ttt gtc gga gtg tct gga gag gag gtg     615
Asp Phe Leu Ile Lys Ser Ser Phe Val Gly Val Ser Gly Glu Glu Val
         45                  50                  55 tgg ttc gat gag aag ggg gat gct ccc gga agg tat gac att atg aat     663
Trp Phe Asp Glu Lys Gly Asp Ala Pro Gly Arg Tyr Asp Ile Met Asn
     60                  65                  70 ctg cag tac aca gaa gct aat cgc tat gac tat gtc cac gtg ggg acc     711
Leu Gln Tyr Thr Glu Ala Asn Arg Tyr Asp Tyr Val His Val Gly Thr
 75                  80                  85                  90 tgg cat gaa gga gtg ctg aat att gat gat tac aaa atc cag atg aac     759
```

```
                  Trp His Glu Gly Val Leu Asn Ile Asp Asp Tyr Lys Ile Gln Met Asn
                                   95                  100                 105 aaa agc gga atg gta cga tct gtg tgc agt gag cct tgc tta aag ggt              807
Lys Ser Gly Met Val Arg Ser Val Cys Ser Glu Pro Cys Leu Lys Gly
            110                 115                 120 cag att aag gtc ata cgg aaa gga gaa gtg agc tgc tgc tgg atc tgc              855
Gln Ile Lys Val Ile Arg Lys Gly Glu Val Ser Cys Cys Trp Ile Cys
            125                 130                 135 acg gcc tgc aaa gag aat gag ttt gtg cag gac gag ttc acc tgc aga              903
Thr Ala Cys Lys Glu Asn Glu Phe Val Gln Asp Glu Phe Thr Cys Arg
        140                 145                 150 gcc tgt gac ctg ggg tgg tgg ccc aac gca gag ctc aca ggc tgt gag              951
Ala Cys Asp Leu Gly Trp Trp Pro Asn Ala Glu Leu Thr Gly Cys Glu
155                 160                 165                 170 ccc att cct gtc cgt tat ctt gag tgg agt gac ata gaa tct atc ata              999
Pro Ile Pro Val Arg Tyr Leu Glu Trp Ser Asp Ile Glu Ser Ile Ile
                175                 180                 185 gcc atc gcc ttt tct tgc ctg ggc atc ctc gtg acg ctg ttt gtc acc             1047
Ala Ile Ala Phe Ser Cys Leu Gly Ile Leu Val Thr Leu Phe Val Thr
            190                 195                 200 ctc atc ttc gtt ctg tac cgg gac aca ccc gtg gtc aaa tcc tcc agt             1095
Leu Ile Phe Val Leu Tyr Arg Asp Thr Pro Val Val Lys Ser Ser Ser
            205                 210                 215 agg gag ctc tgc tat atc att ctg gct ggt att ttc ctc ggc tat gtg             1143
Arg Glu Leu Cys Tyr Ile Ile Leu Ala Gly Ile Phe Leu Gly Tyr Val
        220                 225                 230 tgc cct ttc acc ctc atc gcc aaa cct act acc aca tcc tgc tac ctc             1191
Cys Pro Phe Thr Leu Ile Ala Lys Pro Thr Thr Thr Ser Cys Tyr Leu
235                 240                 245                 250 cag cgc ctc cta gtt ggc ctc tct tct gcc atg tgc tac tct gct tta             1239
Gln Arg Leu Leu Val Gly Leu Ser Ser Ala Met Cys Tyr Ser Ala Leu
                255                 260                 265 gtg acc aaa acc aat cgt att gca cgc atc ctg gct ggc agc aag aag             1287
Val Thr Lys Thr Asn Arg Ile Ala Arg Ile Leu Ala Gly Ser Lys Lys
            270                 275                 280 aag atc tgc acc cgg aag ccc aga ttc atg agc gct tgg gcc caa gtg             1335
Lys Ile Cys Thr Arg Lys Pro Arg Phe Met Ser Ala Trp Ala Gln Val
            285                 290                 295 atc ata gcc tcc att ctg att agt gta cag cta aca cta gtg gtg acc             1383
Ile Ile Ala Ser Ile Leu Ile Ser Val Gln Leu Thr Leu Val Val Thr
        300                 305                 310 ttg atc atc atg gag cct ccc atg ccc att ttg tcc tac ccg agt atc             1431
Leu Ile Ile Met Glu Pro Pro Met Pro Ile Leu Ser Tyr Pro Ser Ile
315                 320                 325                 330 aag gaa gtc tac ctt atc tgc aat acc agc aac ctg ggt gta gtg gcc             1479
Lys Glu Val Tyr Leu Ile Cys Asn Thr Ser Asn Leu Gly Val Val Ala
                335                 340                 345 cct gtg ggt tac aat gga ctc ctc atc atg agc tgt acc tac tat gcc             1527
Pro Val Gly Tyr Asn Gly Leu Leu Ile Met Ser Cys Thr Tyr Tyr Ala
            350                 355                 360 ttc aag acc cgc aac gtg ccg gcc aac ttc aat gag gct aaa tac atc             1575
Phe Lys Thr Arg Asn Val Pro Ala Asn Phe Asn Glu Ala Lys Tyr Ile
            365                 370                 375 gcc ttc acc atg tac act acc tgc atc atc tgg ctg gct ttc gtt ccc             1623
Ala Phe Thr Met Tyr Thr Thr Cys Ile Ile Trp Leu Ala Phe Val Pro
        380                 385                 390 att tac ttt ggg agc aac tac aag atc atc act acc tgc ttc gcg gtg             1671
Ile Tyr Phe Gly Ser Asn Tyr Lys Ile Ile Thr Thr Cys Phe Ala Val
395                 400                 405                 410
```

-continued

```
agc ctc agt gtg acg gtg gcc ctg ggg tgc atg ttt act ccg aag atg   1719
Ser Leu Ser Val Thr Val Ala Leu Gly Cys Met Phe Thr Pro Lys Met
            415                 420                 425 tac atc atc att gcc aaa cct gag agg aac gtc cgc agt gcc ttc acg   1767
Tyr Ile Ile Ile Ala Lys Pro Glu Arg Asn Val Arg Ser Ala Phe Thr
        430                 435                 440 acc tct gat gtt gtc cgc atg cac gtc ggt gat ggc aaa ctg ccg tgc   1815
Thr Ser Asp Val Val Arg Met His Val Gly Asp Gly Lys Leu Pro Cys
    445                 450                 455 cgc tcc aac acc ttc ctc aac att ttc cgg aga aag aag ccc ggg gca   1863
Arg Ser Asn Thr Phe Leu Asn Ile Phe Arg Arg Lys Lys Pro Gly Ala
460                 465                 470 ggg aat gcc aag aag agg cag cca gaa ttc tcg ccc agc agc cag tgt   1911
Gly Asn Ala Lys Lys Arg Gln Pro Glu Phe Ser Pro Ser Ser Gln Cys
475                 480                 485                 490 ccg tcg gca cat gcg cag ctt tga aaacccccac actgcagtga atgt        1959
Pro Ser Ala His Ala Gln Leu
                495
```

<210> SEQ ID NO 8
<211> LENGTH: 497
<212> TYPE: PRT
<213> ORGANISM: Rattus norvegicus

<400> SEQUENCE: 8

```
Met Gly Phe Val Ile Asn Ala Ile Tyr Ala Met Ala His Gly Leu Gln
1               5                   10                  15

Asn Met His His Ala Leu Cys Pro Gly His Val Gly Leu Cys Asp Ala
            20                  25                  30

Met Lys Pro Ile Asp Gly Arg Lys Leu Leu Asp Phe Leu Ile Lys Ser
        35                  40                  45

Ser Phe Val Gly Val Ser Gly Glu Glu Val Trp Phe Asp Glu Lys Gly
    50                  55                  60

Asp Ala Pro Gly Arg Tyr Asp Ile Met Asn Leu Gln Tyr Thr Glu Ala
65                  70                  75                  80

Asn Arg Tyr Asp Tyr Val His Val Gly Thr Trp His Glu Gly Val Leu
                85                  90                  95

Asn Ile Asp Asp Tyr Lys Ile Gln Met Asn Lys Ser Gly Met Val Arg
            100                 105                 110

Ser Val Cys Ser Glu Pro Cys Leu Lys Gly Gln Ile Lys Val Ile Arg
        115                 120                 125

Lys Gly Glu Val Ser Cys Cys Trp Ile Cys Thr Ala Cys Lys Glu Asn
    130                 135                 140

Glu Phe Val Gln Asp Glu Phe Thr Cys Arg Ala Cys Asp Leu Gly Trp
145                 150                 155                 160

Trp Pro Asn Ala Glu Leu Thr Gly Cys Glu Pro Ile Pro Val Arg Tyr
                165                 170                 175

Leu Glu Trp Ser Asp Ile Glu Ser Ile Ile Ala Ile Ala Phe Ser Cys
            180                 185                 190

Leu Gly Ile Leu Val Thr Leu Phe Val Thr Leu Ile Phe Val Leu Tyr
        195                 200                 205

Arg Asp Thr Pro Val Val Lys Ser Ser Ser Arg Glu Leu Cys Tyr Ile
    210                 215                 220

Ile Leu Ala Gly Ile Phe Leu Gly Tyr Val Cys Pro Phe Thr Leu Ile
225                 230                 235                 240

Ala Lys Pro Thr Thr Thr Ser Cys Tyr Leu Gln Arg Leu Leu Val Gly
                245                 250                 255
```

-continued

Leu Ser Ser Ala Met Cys Tyr Ser Ala Leu Val Thr Lys Thr Asn Arg
            260                 265                 270

Ile Ala Arg Ile Leu Ala Gly Ser Lys Lys Ile Cys Thr Arg Lys
            275                 280                 285

Pro Arg Phe Met Ser Ala Trp Ala Gln Val Ile Ile Ala Ser Ile Leu
            290                 295                 300

Ile Ser Val Gln Leu Thr Leu Val Val Thr Leu Ile Ile Met Glu Pro
305                 310                 315                 320

Pro Met Pro Ile Leu Ser Tyr Pro Ser Ile Lys Glu Val Tyr Leu Ile
                    325                 330                 335

Cys Asn Thr Ser Asn Leu Gly Val Val Ala Pro Val Gly Tyr Asn Gly
                340                 345                 350

Leu Leu Ile Met Ser Cys Thr Tyr Tyr Ala Phe Lys Thr Arg Asn Val
                355                 360                 365

Pro Ala Asn Phe Asn Glu Ala Lys Tyr Ile Ala Phe Thr Met Tyr Thr
            370                 375                 380

Thr Cys Ile Ile Trp Leu Ala Phe Val Pro Ile Tyr Phe Gly Ser Asn
385                 390                 395                 400

Tyr Lys Ile Ile Thr Thr Cys Phe Ala Val Ser Leu Ser Val Thr Val
                    405                 410                 415

Ala Leu Gly Cys Met Phe Thr Pro Lys Met Tyr Ile Ile Ile Ala Lys
                420                 425                 430

Pro Glu Arg Asn Val Arg Ser Ala Phe Thr Thr Ser Asp Val Val Arg
            435                 440                 445

Met His Val Gly Asp Gly Lys Leu Pro Cys Arg Ser Asn Thr Phe Leu
            450                 455                 460

Asn Ile Phe Arg Arg Lys Lys Pro Gly Ala Gly Asn Ala Lys Lys Arg
465                 470                 475                 480

Gln Pro Glu Phe Ser Pro Ser Ser Gln Cys Pro Ser Ala His Ala Gln
                    485                 490                 495

Leu

<210> SEQ ID NO 9
<211> LENGTH: 2948
<212> TYPE: DNA
<213> ORGANISM: Rattus norvegicus

<400> SEQUENCE: 9
agaaaaaaag ttttctactg ctccttgatg atttatttca taaaaatctt aattttgaac      60
tctatgctgt ttactctata acataaaatc tttactaaat aaagaaggaa accaggaaat     120
aactgttttc agacagaata taatagtcgg tcacaagtac aaaacaagct ctgctttccc     180
caatgtcatg atccctgtca gagtctgaag cccctgaaat cactgagcac tgggctctgg     240
atattgaggg tatagccctg actggattct tatttgtcac cctggtagtg atctgttttt     300
attgttacag gaaatgaaag cttggaagaa aactatgtcc aggacagcaa atgggatttt     360
gtcatcaatg ccatctatgc catggcacat gggctgcaga acatgcacca tgctctgtgt     420
cccggccatg tgggcctgtg tgatgctatg aaacccattg atggcaggaa gctcctggat     480
ttcctcatca atcctctttt tgtcggagtg tctggagagg aggtgtggtt cgatgagaag     540
ggggatgctc ccggaaggta tgacattatg aatctgcagt acacagaagc taatcgctat     600
gactatgtcc acgtggggac ctggcatgaa ggagtgctga atattgatga ttacaaaatc     660
cagatgaaca aaagcggaat ggtacgatct gtgtgcagtg agccttgctt aaagggtcag     720

-continued

```
attaaggtca tacggaaagg agaagtgagc tgctgctgga tctgcacggc ctgcaaagag      780
aatgagtttg tgcaggacga gttcacctgc agagcctgtg acctggggtg gtggcccaac      840
gcagagctca caggctgtga gcccattcct gtccgttatc ttgagtggag tgacatagaa      900
tctatcatag ccatcgcctt ttcttgcctg ggcatcctcg tgacgctgtt tgtcaccctc      960
atcttcgttc tgtaccggga cacaccgtg gtcaaatcct ccagtaggga gctctgctat     1020
atcattctgg ctggtatttt cctcggctat gtgtgcccct tcaccctcat cgccaaacct     1080
actaccacat cctgctacct ccagcgcctc ctagttggcc tctcttctgc catgtgctac     1140
tctgctttag tgaccaaaac caatcgtatt gcacgcatcc tggctggcag caagaagaag     1200
atctgcaccc ggaagcccag attcatgagc gcttgggccc aagtgatcat agcctccatt     1260
ctgattagtg tacagctaac actagtggtg accttgatca tcatggagcc tcccatgccc     1320
attttgtcct acccgagtat caaggaagtc taccttatct gcaataccag caacctgggt     1380
gtagtggccc ctgtgggtta caatggactc ctcatcatga gctgtaccta ctatgccttc     1440
aagacccgca acgtgccggc caacttcaat gaggctaaat acatcgcctt caccatgtac     1500
actacctgca tcatctggct ggctttcgtt cccatttact ttgggagcaa ctacaagatc     1560
atcactacct gcttcgcggt gagcctcagt gtgacggtgg ccctggggtg catgtttact     1620
ccgaagatgt acatcatcat tgccaaacct gagaggaacg tccgcagtgc cttcacgacc     1680
tctgatgttg tccgcatgca cgtcggtgat ggcaaactgc cgtgccgctc aacaccttc      1740 ctcaacattt tccggagaaa gaagcccggg gcagggaatg ccaattctaa cggcaagtct     1800
gtgtcatggt ctgaaccagg tggaagacag gcgcccaagg acagcacgt gtggcagcgc      1860 ctctctgtgc acgtgaagac caacgagacg gcctgtaacc aaacagccgt aatcaaaccc     1920
ctcactaaaa gttaccaagg ctctggcaag agcctgacct tttcagatgc cagcaccaag     1980
acccttacta atgtggaaga agaggacaat accccttctg ctcacttcag ccctcccagc     2040
agcccttcta tggtggtgca ccgacgcggg ccacccgtgg ccaccacacc acctctgcca     2100
ccccatctga ccgcagaaga gacccccctg ttcctggctg attccgtcat ccccaagggc     2160
ttgcctcctc ctctcccgca gcagcagcca cagcagccgc cccctcagca gccccccgcag   2220 cagcccaagt ccctgatgga ccagctgcaa ggcgtagtca ccaacttcgg ttcgggggatt    2280 ccagatttcc atgcggtgct ggcaggcccg gggacaccag aaacagcct gcgctctctg      2340 tacccgcccc cgcctccgcc gcaacacctg cagatgctgc cctgcacct gagcaccttc      2400 caggaggagt ccatctcccc tcctggggag acatcgatg atgacagtga gagattcaag      2460
ctcctgcagg agttcgtgta cgagcgcgaa gggaacaccg aagaagatga attggaagag     2520
gaggaggacc tgcccacagc cagcaagctg acccctgagg attctcctgc cctgacgcct    2580
ccttctcctt tccgagattc cgtggcctct ggcagctcag tgcccagttc ccccgtatct    2640
gagtcggtcc tctgcacccc tccaaatgta acctacgcct ctgtcattct gagggactac    2700
aagcaaagct cttccaccct gtagtgtgtg tgtgtgtgtg ggggcggggg gagtgcgcat    2760
ggagaagcca gagatgccaa ggagtgtcaa cccttccaga aatgtgtaga aagcagggtg    2820
agggatgggg atggaggacc acggtctgca gggaagaaaa aaaaaatgct gcggctgcct    2880
taaagaagga gagggacgat gccaactgaa cagtggtcct ggccaggatt gtgactcttg    2940
aattattc                                                             2948
```

<210> SEQ ID NO 10

<211> LENGTH: 1869
<212> TYPE: DNA
<213> ORGANISM: Rattus norvegicus

<400> SEQUENCE: 10

```
agaaaaaaag ttttctactg ctccttgatg atttatttca taaaaatctt aattttgaac    60
tctatgctgt ttactctata acataaaatc tttactaaat aaagaaggaa accaggaaat   120
aactgttttc agacagaata taatagtcgg tcacaagtac aaaacaagct ctgctttccc   180
caatgtcatg atccctgtca gagtctgaag cccctgaaat cactgagcac tgggctctgg   240
atattgaggg tatagccctg actggattct tatttgtcac cctggtagtg atctgttttt   300
attgttacag gaaatgaaag cttggaagaa aactatgtcc aggacagcaa atgggattt    360
gtcatcaatg ccatctatgc catggcacat gggctgcaga acatgcacca tgctctgtgt   420
cccggccatg tgggcctgtg tgatgctatg aaacccattg atggcaggaa gctcctggat   480
ttcctcatca atcctctttt tgtcggagtg tctggagagg aggtgtggtt cgatgagaag   540
ggggatgctc ccggaaggta tgacattatg aatctgcagt acacagaagc taatcgctat   600
gactatgtcc acgtggggac ctggcatgaa ggagtgctga atattgatga ttacaaaatc   660
cagatgaaca aaagcggaat ggtacgatct gtgtgcagtg agccttgctt aaagggtcag   720
attaaggtca tacggaaagg agaagtgagc tgctgctgga tctgcacggc tgcaaagag    780
aatgagtttg tgcaggacga gttcacctgc agagcctgtg acctggggtg gtggcccaac   840
gcagagctca caggctgtga gcccattcct gtccgttatc ttgagtggag tgacatagaa   900
tctatcatag ccatcgcctt ttcttgcctg gcatcctcg tgacgctgtt tgtcaccctc   960
atcttcgttc tgtaccggga cacccccgtg gtcaaatcct ccagtaggga gctctgctat  1020
atcattctgg ctggtatttt cctcggctat gtgtgcccct tcaccctcat cgccaaacct  1080
actaccacat cctgctacct ccagcgcctc ctagttggcc tctcttctgc catgtgctac  1140
tctgctttag tgaccaaaac caatcgtatt gcacgcatcc tggctggcag caagaagaag  1200
atctgcaccc ggaagcccag attcatgagc gcttgggccc aagtgatcat agcctccatt  1260
ctgattagtg tacagctaac actagtggtg accttgatca tcatggagcc tcccatgccc  1320
attttgtcct acccgagtat caaggaagtc taccttatct gcaataccag caacctgggt  1380
gtagtggccc ctgtgggtta caatggactc ctcatcatga gctgtaccta ctatgccttc  1440
aagacccgca acgtgccggc caacttcaat gaggctaaat acatcgcctt caccatgtac  1500
actacctgca tcatctggct ggctttcgtt cccatttact ttgggagcaa ctacaagatc  1560
atcactacct gcttcgcggt gagcctcagt gtgacggtgg ccctggggtg catgtttact  1620
ccgaagatgt acatcatcat tgccaaacct gagaggaacg tccgcagtgc cttcacgacc  1680
tctgatgttg tccgcatgca cgtcggtgat ggcaaactgc cgtgccgctc caacaccttc  1740
ctcaacattt tccggagaaa gaagcccggg cagggaatgc caagaagag gcagccagaa   1800
ttctcgccca gcagccagtg tccgtcggca catgcgcagc tttgaaaacc cccacactgc  1860
agtgaatgt                                                          1869
```

<210> SEQ ID NO 11
<211> LENGTH: 23
<212> TYPE: DNA
<213> ORGANISM: Artificial
<220> FEATURE:
<223> OTHER INFORMATION: primer, mGluR1-718-2F

<400> SEQUENCE: 11
gtgaatcaga ggaagtgttc aga					23

<210> SEQ ID NO 12
<211> LENGTH: 24
<212> TYPE: DNA
<213> ORGANISM: Artificial
<220> FEATURE:
<223> OTHER INFORMATION: primer, mGluR1-718-3F

<400> SEQUENCE: 12
aatgtaacag tcactggtgc tggg					24

<210> SEQ ID NO 13
<211> LENGTH: 23
<212> TYPE: DNA
<213> ORGANISM: Artificial
<220> FEATURE:
<223> OTHER INFORMATION: primer, mGluR1-790-1F

<400> SEQUENCE: 13
gggactctct cctgtcttgt gag					23

<210> SEQ ID NO 14
<211> LENGTH: 23
<212> TYPE: DNA
<213> ORGANISM: Artificial
<220> FEATURE:
<223> OTHER INFORMATION: primer, mGluR1-790-2F

<400> SEQUENCE: 14
agcataacag ggaattgcag tgg					23

<210> SEQ ID NO 15
<211> LENGTH: 23
<212> TYPE: DNA
<213> ORGANISM: Artificial
<220> FEATURE:
<223> OTHER INFORMATION: primer, mGluR1-1599-200F

<400> SEQUENCE: 15
cagacagaat ataatagtcg gtc					23

<210> SEQ ID NO 16
<211> LENGTH: 22
<212> TYPE: DNA
<213> ORGANISM: Artificial
<220> FEATURE:
<223> OTHER INFORMATION: primer, mGluR1-1599-221F

<400> SEQUENCE: 16
acaagtacaa aacaagctct gc					22

<210> SEQ ID NO 17
<211> LENGTH: 25
<212> TYPE: DNA
<213> ORGANISM: Artificial
<220> FEATURE:
<223> OTHER INFORMATION: primer, mGluR1-4253R

<400> SEQUENCE: 17
taccatatgg aattgtgctt tgtca					25

<210> SEQ ID NO 18
<211> LENGTH: 25
<212> TYPE: DNA

```
<213> ORGANISM: Artificial
<220> FEATURE:
<223> OTHER INFORMATION: primer, mGluR1-4198R

<400> SEQUENCE: 18
ataattcaag agtcacaatc ctggc                                              25

<210> SEQ ID NO 19
<211> LENGTH: 23
<212> TYPE: DNA
<213> ORGANISM: Artificial
<220> FEATURE:
<223> OTHER INFORMATION: primer, mGluR1-3266R

<400> SEQUENCE: 19
gggtattgtc ctcttcttcc aca                                                23

<210> SEQ ID NO 20
<211> LENGTH: 23
<212> TYPE: DNA
<213> ORGANISM: Artificial
<220> FEATURE:
<223> OTHER INFORMATION: primer, mGluR1-50F

<400> SEQUENCE: 20
gagaccaata gctgtgtcta ccc                                                23

<210> SEQ ID NO 21
<211> LENGTH: 23
<212> TYPE: DNA
<213> ORGANISM: Artificial
<220> FEATURE:
<223> OTHER INFORMATION: Primer, mGluR1-114F

<400> SEQUENCE: 21
tggacacctg atccacacac ctt                                                23
```